United States Patent
Huang et al.

(10) Patent No.: US 10,231,619 B2
(45) Date of Patent: Mar. 19, 2019

(54) SYSTEMS AND METHODS TO REMOVE SHADOWGRAPHIC FLOW PROJECTIONS IN OCT ANGIOGRAPHY

(71) Applicant: OREGON HEALTH & SCIENCE UNIVERSITY, Portland, OR (US)

(72) Inventors: David Huang, Portland, OR (US); Yali Jia, Portland, OR (US); Miao Zhong, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/374,872

(22) Filed: Dec. 9, 2016

(65) Prior Publication Data
US 2017/0169590 A1 Jun. 15, 2017

Related U.S. Application Data

(60) Provisional application No. 62/265,305, filed on Dec. 9, 2015.

(51) Int. Cl.
| | | |
|---|---|---|
| *A61B 3/12* | (2006.01) | |
| *G06T 5/00* | (2006.01) | |
| *A61B 3/10* | (2006.01) | |
| *A61B 3/00* | (2006.01) | |

(52) U.S. Cl.
CPC .......... *A61B 3/1241* (2013.01); *A61B 3/0025* (2013.01); *A61B 3/102* (2013.01); *G06T 5/002* (2013.01); *G06T 2207/10101* (2013.01); *G06T 2207/20182* (2013.01); *G06T 2207/30041* (2013.01); *G06T 2207/30104* (2013.01)

(58) Field of Classification Search
CPC ..... A61B 3/102; A61B 3/0025; A61B 5/0066; A61B 3/1233; A61B 3/1241; A61B 3/12; A61B 8/10; G06T 2207/30041; G06T 2207/10101; G06T 7/0012; G06T 5/008; G06T 2207/20182; G06T 2211/404; G06T 5/002; G06T 11/008; G06T 2207/10136
See application file for complete search history.

(56) References Cited

U.S. PATENT DOCUMENTS

| | | | | |
|---|---|---|---|---|
| 2003/0161527 | A1* | 8/2003 | Wang | G06K 9/0014 382/156 |
| 2011/0038517 | A1* | 2/2011 | Mistretta | A61B 6/02 382/128 |
| 2012/0274898 | A1* | 11/2012 | Sadda | A61B 3/102 351/206 |
| 2013/0289882 | A1* | 10/2013 | Sharma | A61B 3/102 702/19 |
| 2013/0301000 | A1* | 11/2013 | Sharma | A61B 3/102 351/206 |
| 2014/0073917 | A1* | 3/2014 | Huang | A61B 5/0066 600/427 |

(Continued)

*Primary Examiner* — Jingge Wu
(74) *Attorney, Agent, or Firm* — Schwabe, Williamson & Wyatt, P.C.

(57) ABSTRACT

Methods and systems for suppressing shadowgraphic flow projection artifacts in OCT angiography images of a sample are disclosed. In one example approach, normalized OCT angiography data is analyzed at the level of individual A-scans to classify signals as either flow or projection artifact. This classification information is then used to suppress projection artifacts in the three dimensional OCT angiography dataset.

22 Claims, 16 Drawing Sheets

(56) References Cited

U.S. PATENT DOCUMENTS

| | | | | |
|---|---|---|---|---|
| 2014/0228681 A1* | 8/2014 | Jia | ............... | G01B 9/02091 600/425 |
| 2015/0092195 A1* | 4/2015 | Blatter | ............... | G01B 9/02091 356/479 |
| 2016/0000320 A1* | 1/2016 | Sharma | ............... | A61B 3/102 351/206 |
| 2016/0040977 A1* | 2/2016 | An | ............... | G01B 9/02077 356/479 |
| 2016/0242638 A1* | 8/2016 | Durbin | ............... | A61B 3/0025 |
| 2016/0284085 A1* | 9/2016 | Huang | ............... | G06T 7/0016 |
| 2016/0317016 A1* | 11/2016 | Oishi | ............... | A61B 3/102 |
| 2016/0317020 A1* | 11/2016 | Liu | ............... | G01B 9/02076 |
| 2016/0317026 A1* | 11/2016 | Fingler | ............... | A61B 3/102 |
| 2016/0317027 A1* | 11/2016 | Goto | ............... | A61B 3/102 |
| 2017/0020387 A1* | 1/2017 | Fingler | ............... | A61B 3/102 |
| 2017/0035286 A1* | 2/2017 | Meyer | ............... | A61B 3/102 |
| 2017/0055830 A1* | 3/2017 | Kotoku | ............... | A61B 3/1233 |
| 2017/0065170 A1* | 3/2017 | Yamashita | ............... | A61B 3/102 |
| 2017/0105618 A1* | 4/2017 | Schmoll | ............... | A61B 3/102 |
| 2017/0164825 A1* | 6/2017 | Chen | ............... | A61B 3/102 |
| 2018/0014728 A1* | 1/2018 | An | ............... | G06T 7/0014 |
| 2018/0055355 A1* | 3/2018 | Sarunic | ............... | A61B 3/1233 |

\* cited by examiner

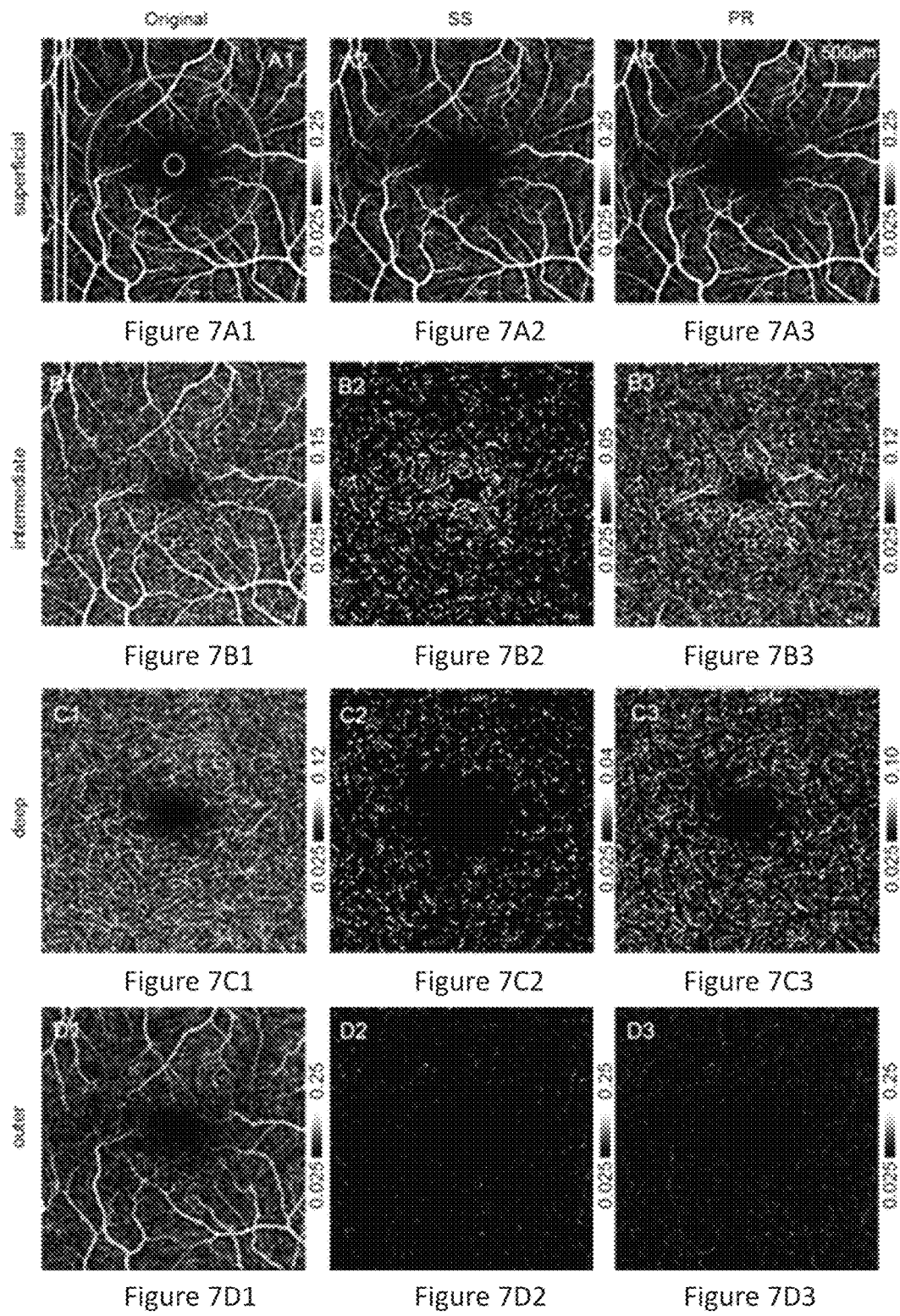
Figure 7A1  Figure 7A2  Figure 7A3
Figure 7B1  Figure 7B2  Figure 7B3
Figure 7C1  Figure 7C2  Figure 7C3
Figure 7D1  Figure 7D2  Figure 7D3

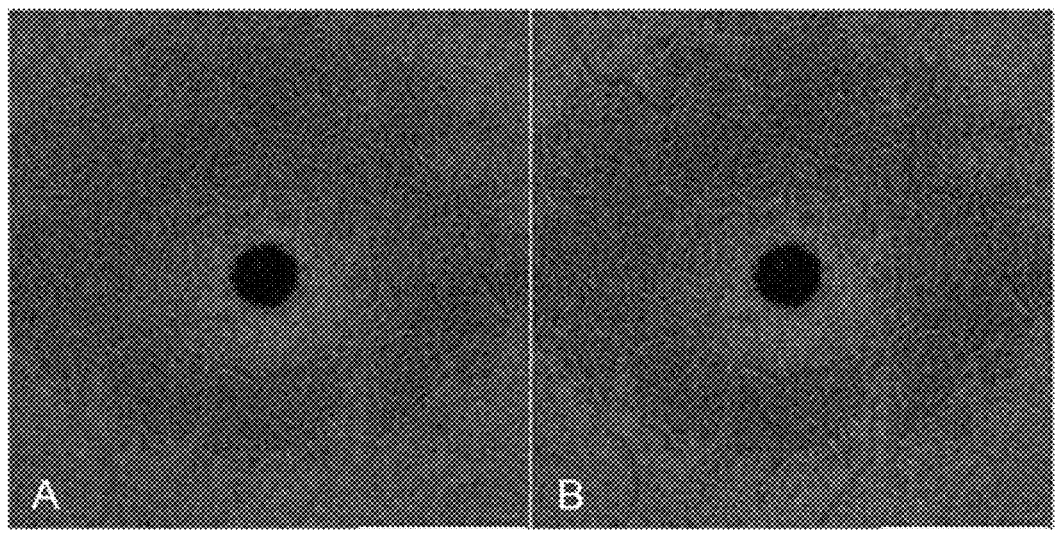
Figure 8A                    Figure 8B

SYSTEMS AND METHODS TO REMOVE SHADOWGRAPHIC FLOW PROJECTIONS IN OCT ANGIOGRAPHY

CROSS REFERENCE TO RELATED APPLICATION

The present application claims priority to U.S. Provisional Patent Application No. 62/265,305, titled "SYSTEMS AND METHODS TO REMOVE SHADOGRAPHIC FLOW PROJECTIONS IN OCT ANGIOGRAPHY," filed Dec. 9, 2015, the disclosure of which is hereby incorporated by reference in its entirety.

ACKNOWLEDGEMENT OF GOVERNMENT SUPPORT

This invention was made with the support of the United States government under the terms of Grant Numbers R01 EY023285, R01 EY024544, and DK104397 awarded by the National Institutes of Health. The United States government has certain rights in this invention.

FIELD

Generally, the field involves methods of using optical coherence tomography (OCT) in angiography. More specifically, the field involves methods of processing OCT angiography data to remove shadowgraphic flow projections.

BACKGROUND

Optical coherence tomography (OCT) is a noninvasive, depth resolved, volumetric imaging technique that uses principles of interferometry to provide cross-sectional and three-dimensional (3D) imaging of biological tissues. OCT offers millimeter level penetration of tissues with micrometer-scale axial and lateral resolution and is thus well-suited to imaging tissue microstructure. In ophthalmology OCT has become a part of the standard of care and is commonly used to visualize retinal morphology. In recent years OCT methods have been extended to allow visualization of blood flow within tissues and to separate these flow regions from their surrounding tissue microstructure. When applied at the microcirculation level, OCT-based flow imaging techniques are termed "OCT angiography." Because the retina is organized into distinct layers with separate microvascular beds as well as layers with no vasculature, OCT angiography holds great promise as a clinical tool for analyzing vascular health and pathology in the eye.

OCT angiography (OCT-A) employs the motion of red blood cells (RBCs) as intrinsic contrast, providing high resolution maps of microvascular networks (Wang R et al, Opt Express 15, 4083-4097 (2007); Makita F et al, Opt Express 15, 1271-1283 (2011); incorporated by reference herein). Specifically, OCT angiography algorithms detect decorrelation values in structural OCT signal intensity or phase across pixels over time to separate blood flow from static tissue. Split-spectrum amplitude-decorrelation angiography (SSADA) is an example of an OCT angiography algorithm used in commercial systems. The 3D datasets produced by OCT angiography algorithms have a one-to-one correspondence to the structural OCT images (i.e., they are registered), and therefore, can be used to present the blood flow associated with specific structural features of the tissue under examination. For example, by segmenting the various tissue layers with the 3D dataset and generating 2D en face angiograms (described below), it is possible distinguish between the normal retinal circulation and choroidal circulation, and highlight abnormal neovascularization in the vitreous or outer retina.

A standard method of presenting OCT angiography data is the generation of a 2D en face angiogram, wherein decorrelation data from a three-dimensional "slab" of a given thickness from the dataset is projected onto a 2D plane for viewing (for instance, the voxel set bounded by the inner limiting membrane and the inner nuclear layer may be projected to produce a 2D en face angiogram of the inner retina). These 2D en face angiograms can be interpreted in a manner similar to traditional angiography techniques such as fluorescein angiography (FA) or indocyanine green (ICG) angiography, and are thus well-suited for clinical use. Furthermore, OCT angiography eliminates the risk and reduces the time associated with the dye injections used in FA and ICG procedures (Jia Y et al, Proc Natl Acad Sci USA 112, E2395-2402 (2015); Lopez-Saez M et al, Ann Allergy Asthma Immunol 81, 428-430 (1998); incorporated by reference herein), making it more accessible for clinical use than FA or ICG, and allowing for better visualization of retinal capillaries.

A limitation of OCT angiography, however, is that the visualization of deeper vascular networks is impeded by a shadowgraphic flow projection artifact, which arises from fluctuating shadows cast in the depth direction by flowing blood cells in the more superficial vessels. The shadowgraphic projection results in variation of both amplitude and phase, and can be picked up by most OCT angiography algorithms as false flow, also called projection artifact. On cross-sectional angiograms, the projection artifact appears as elongated flow signals (tails) below blood vessels, which effectively reduces the depth resolution of OCT angiography. On en face angiograms, the projection artifact causes superficial vascular networks to be duplicated on deeper slabs. One clinical problem caused by this artifact is the duplication of normal inner retinal vascular pattern onto the outer retinal slab, which clutters the deeper slab and interferes with the detection and measurement of choroidal neovascularization (CNV) (Braaf K et al, Biomed Opt Express 4, 51-65 (2013); de Carlo T et al, Int J Retina and Vitreous 1, 5 (2015); Dansingani K et al, Eye 29, 703-706 (2015); Spaide R et al, JAMA Ophth 133, 66-73 (2015); Hendargo H et al, Biomed Opt Express 4, 803-821 (2013); Huang Y et al, Biomed Opt Express 6, 1195-1208 (2015); Spaide R et al, Retina 35, 2163-2180 (2015); incorporated by reference herein). Since CNV is the most serious complication of age-related neovascularization (AMD), the leading cause of blindness in the US (Pascolini D et al, Neuro-Ophthalmol 11, 67-115 (2004); EDPR Group, Arch Ophthalmol 122, 477 (2004); Braaf K et al, Biomed Opt Express 4, 51-65 (2013); Ferris F et al, Arch Ophthalmol 102, 1640-1642 (1984); incorporated by reference herein), the flow projection artifact is a problem of great clinical significance.

In commercial OCT angiography and previous work, a slab-subtraction (SS) algorithm has been used to suppress the flow projection artifact. For example, the vascular pattern of the inner retinal circulation can be subtracted from the outer retinal slab, leaving the outer retinal slab vessel-free (as it is known to be in the healthy eye) (Liu L et al, Biomed Opt Express 6, 3564-3576 (2015); Zhang A et al, Biomed Opt Express 6, 4130-4143 (2015); incorporated by reference herein). Unfortunately, the SS algorithm replaces the flow projection artifact with a shadow artifact, the problem of which becomes obvious when one examines a CNV case. The SS algorithm erases most of the CNV that overlaps with the more superficial retinal circulation, leaving gaps that compromise the vascular integrity (i.e., connectivity) and are difficult to reconstruct (Huang D et al, *OCT Angiography Atlas,* 2015; incorporated by reference herein). Another shortcoming of the SS approach is that it is only operates on 2D en face angiograms; but does not provide correction to cross sectional B-scan images. In other words, the SS algorithm is that it does not suppress flow projection through the depth direction of the slab, leaving obvious tail artifacts on cross-sectional OCT angiograms. Thus, this approach cannot be used to delineate separate vascular plexuses without pre-defining their slab boundaries. Previous histological studies have shown that there are as many as 3 distinct vascular plexuses in the inner retina alone (Chan G et al, *Invest Ophthalmol Vis Sci* 53, 5502-5514 (2012); incorporated by reference herein). It is difficult to delineate these 3 plexuses in vivo using the SS algorithm. All of these deficiencies underscore the need for a more robust method of processing 3D datasets to remove shadowgraphic flow projection artifact.

BRIEF DESCRIPTION OF THE DRAWINGS

FIG. 1A shows the composite B-scan image before shadowgraphic flow projections artifacts are suppressed. FIG. 1B shows the composite B-scan image after shadowgraphic flow projections artifacts are suppressed.

FIG. 5A shows composite cross-sectional OCT-A before projection suppression. This 0.23 mm wide example is taken from the parafoveal region. The decorrelation signal is overlaid on the structural OCT (log reflectance amplitude). The projection artifacts are notable as tails trailing below the real vessels and projected onto deeper high-reflectance layers. FIG. 5B shows the original decorrelation and log reflectance amplitude values of the A-line pointed to by the arrow in A. FIG. 5C shows reflectance-normalized decorrelation values according to equation 1. Four successively higher peaks (green arrows) on this plot represent in-situ flow in real vessels. FIG. 5D shows a plot of the decorrelation values after clean up by the PR algorithm—decorrelation values outside the successive peaks represented projection artifacts and were set to zero. FIG. 5E shows a composite cross-sectional OCT-A image after clean-up of projection artifacts using the PR algorithm. The arrows are pointed at the same voxels identified as real vessels in FIGS. 5C and 5D. Note that 4 vessels co-existing along the same A-line could be identified on the PR OCT-A, and their axial positions could be pinpointed. The PR OCT-A of the macula show 3 distinct vascular plexuses in the inner retina—superficial, intermediate, and deep—as has been described in previous histological studies.

FIG. 6A shows a histology image of a nonhuman primate retina, where the white holes represent blood vessels in the inner retina. FIG. 6B shows a composite B-scan OCT angiography image, where the blood vessels can also be visualized and divided into three unique layers. The top dashed line represents the vitreous/ILM boundary. The second and third dashed lines represent 9 µm above and below the inner plexiform layer (IPL)/inner nuclear layer (INL) interface, and the fourth (bottom) dashed line represents the outer plexiform layer (OPL)/outer nuclear layer (ONL) interface.

FIGS. 7A1-7D3 shows a comparison of Retinal OCT-A processed without projection suppression (Original, Column 1), with projection suppressed by the standard slab-subtraction method (SS, Column 2), and with the novel projection-resolved algorithm (PR, Column 3). Row A: En face OCT-A of the superficial vascular plexus. Row B: En face OCT-A of the intermediate capillary plexus. Row C: En face OCT-A of the deep capillary plexus. Row D: En face OCT-A of the outer retinal slab. In A1, the rectangle 704 is the region of interest (ROI) of the analysis in FIG. 9. The circles 706 and 708 mark the parafoveal ROI of the vessel density calculation in FIG. 11.

FIGS. 8A and 8B show a frame from an en face fly-through (superficial to deep) video showing 3D OCT-A without projection suppression (FIG. 8A) and with projection artifacts removed using the PR algorithm (FIG. 8B).

FIG. 9A shows individual plots from 13 healthy human study participants. FIG. 9B shows a plot of population mean and standard deviation.

FIGS. 12A-12C2 shows a comparison of projection artifact suppression algorithms in the visualization of choroidal neovascularization (CNV) in a case of neovascular age-related macular degeneration (AMD). FIG. 12A shows en face OCT-A of the outer retinal slab without projection artifact suppression. FIG. 12B1 shows projection suppression with the SS algorithm alone. FIG. 12B2 shows projection suppression with the PR algorithm. FIG. 12C1 shows a saliency-based algorithm that is used to clean up background clutter after SS. FIG. 12C2 shows a saliency-based algorithm that is used to clean up background clutter after PR.

DETAILED DESCRIPTION

Figure 1A:
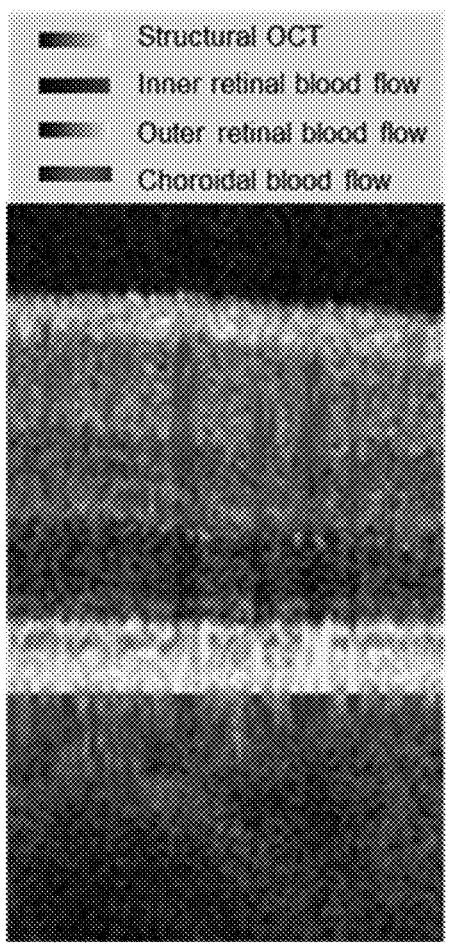
FIGS. 1A and 1B show an example of a composite B-scan image before and after shadowgraphic flow projection suppression. Blood flow data is shown at different depths that correspond to the inner retina layers, outer retina layers, and choroidal layer.

The present disclosure is directed to methods and systems for suppressing shadowgraphic flow projection artifacts in OCT angiography data. The disclosed method, herein termed projection-resolved (PR) OCT angiography, works with both two- and three-dimensional OCT datasets. In a typical embodiment, structural OCT data is received from an OCT scanning device in voxel format and used to calculate a corresponding OCT angiography dataset comprised of decorrelation values. The decorrelation values in the OCT angiography dataset are normalized to account for the relationship between flow projection and intensity in the structural OCT. The normalized signal values are then analyzed along the direction of individual axial scan lines (A-scans) and voxels along the scan line are classified as either flow or as projection artifact. This classification is used to suppress those voxels in the non-normalized OCT angiography dataset identified as projection artifacts. In an embodiment, this suppression may entail setting the decorrelation value of the voxel to zero. Once processed to suppress shadowgraphic flow projection artifacts, the OCT angiography data can be used, for example, to generate 2D en face angiograms, to combine structure and flow information into composite cross sectional B-scan images, to resolve distinct vascular plexuses across the depth of the retina, or to quantify of blood flow within the imaged region.

An aspect of the disclosed PR algorithm is that it operates at the level of individual axial scans (A-scans) in an OCT angiography dataset and can identify multiple vessels along that A-scan without presuming a pre-defined slab boundary or the number of slabs and vessels. Voxels are classified as either flow data or projection artifact based on the normalized intensity profile of the A-scan as a function of scan depth. Specifically, for a given A-scan, decorrelation values are first intensity-normalized and then evaluated in the direction from least to greatest depth to identify voxels whose normalized intensity values are higher than all shallower voxels in the same axial scan line. The intensity values for these identified voxels are retained in the (non-normalized) OCT angiography dataset; all other voxels along the A-scan are regarded as projection artifact and suppressed (for example, set to a zero) in the OCT angiography dataset. All A-scans are processed sequentially in this manner to produce a volumetric OCT angiography dataset within which the shadowgraphic projection artifacts are suppressed, thereby improving the quality and resolution of blood flow information through the depth of the sample.

Compared with the previously described SS algorithm for projection suppression, PR preserves the integrity and continuity of deeper vascular networks (e.g., less loss of vessel connectivity in CNV structures) and provides superior projection suppression on 2D en face angiograms. Because PR is a volumetric technique, shadowgraphic projections on B-scan images are also suppressed, allowing for improved fidelity in blood flow characterization in cross-sectional images of the retinal layers. Such suppression of artifacts in cross sectional images is not achievable using en face-based shadow removal techniques such as SS. Further, PR improves the depth resolution of OCT angiography by removing artifactual projection tails that may appear behind blood vessels. The enhanced depth resolution afforded by PR enables the identification of intermediate and deep retinal capillary plexuses that have previously only been visualized in ex vivo tissue preparations.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample may be obtained using optical coherence tomography (OCT) (structure) and OCT angiography (flow) imaging based on the detection of spectral interference. Such imaging may be two-dimensional (2-D) or three-dimensional (3-D), depending on the application. Structural imaging may be of an extended depth range relative to prior art methods, and flow imaging may be performed in real time. One or both of structural imaging and flow imaging as disclosed herein may be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is directed along the optical axis of the OCT device and penetrates the sample being imaged. The A-scan encodes reflectivity information (for example, signal intensity) as a function of depth.

B-scan: A cross-sectional tomograph that may be achieved by laterally combining a series of axial depth scans (i.e., A-scans). A B-scan encodes planar cross-sectional information from the sample and is typically presented as an image.

Dataset: As used herein, a dataset is an ordered-array representation of stored data values that encodes relative spatial location in row-column-depth (x-y-z) format. In the context of OCT, as used herein, a dataset may be conceptualized as a three dimensional array of voxels, each voxel having an associated value (for example, an intensity value or a decorrelation value). An A-scan corresponds to a set of collinear voxels in the depth (axial) direction of the dataset; a B-scan is made up of set of adjacent A-scans combined in the lateral (row) direction. Such a B-scan may also be referred to as an image, and its constituent voxels referred to as pixels. A collection of adjacent B-scans can be combined in the vertical (column) direction to form a 3D volumetric set of voxel data (or 3D image). The most basic form of a dataset as used herein is a single A-scan. More typically, however, a dataset is comprised of multiple A-scans organized into one or more B-scans. In the systems and methods described herein, the dataset obtained by an OCT scanning device is termed a "structural OCT dataset" whose values may, for example, be complex numbers carrying intensity and phase information. This structural OCT dataset can be used to calculate a corresponding dataset termed an "OCT angiography dataset" of decorrelation values reflecting flow within the imaged sample. There is a one-to-one correspondence between the voxels of the structural OCT dataset and the OCT angiography dataset. Thus, values from the datasets may be "overlaid" to present composite images of structure and flow (e.g., tissue microstructure and blood flow).

Optical coherence tomography (OCT) is an optical signal acquisition and processing method that is capable of capturing micrometer-resolution, two- and three-dimensional images from within optical scattering media, e.g., biological tissue. Optical coherence tomography is based on interferometric techniques and typically employs near-infrared light. The use of relatively long wavelength light allows it to penetrate into the scattering medium. As remarked above, among its many applications, OCT-based ocular imaging has found widespread clinical use and can be performed quickly and easily with minimal expertise. OCT is a noninvasive imaging modality which provides accurate and precise anatomical reproduction of the retinal layers thus is well suited for use in detecting and diagnosing diseases of the retina.

In recent years, OCT techniques have been extended to allow the detection of flow within scattering media, typically using speckle variance, decorrelation, phase-difference, or other approaches. Collectively these techniques are termed "OCT angiography" when applied to the detection of microcirculation within biological tissues. OCT angiography provides the ability to noninvasively map vasculature and microvascular beds within tissues. Applied to the retina, OCT angiography is well suited for visualizing and quantifying the integrity of retinal circulation pathways and for detecting abnormalities in ocular hemodynamics and vascular structure.

OCT angiography algorithms detect decorrelation (speckle variance) in OCT intensity or phase over time within an imaged sample to separate blood flow from static tissue. This speckle variance may be produced directly by the flow of RBCs within vascular structures, or may arise indirectly by flickering shadows cast by the flow in the path of the beam. Thus, during OCT image acquisition blood vessels in the superficial layers of the retina cast shadowgraphic flow projection artifacts onto the deeper layers. These flow projection artifacts cause difficulties with the separation of different capillary plexi located at different depths in the retina, hindering detection of vascular abnormalities that might occur in deeper layers. For instance, pathological choroidal neovascularization in the outer retina may be difficult to discern due to the masking effect of overlying shadowgraphic flow projection artifacts from the vasculature of the more superficial inner retina.

Figure 1B:
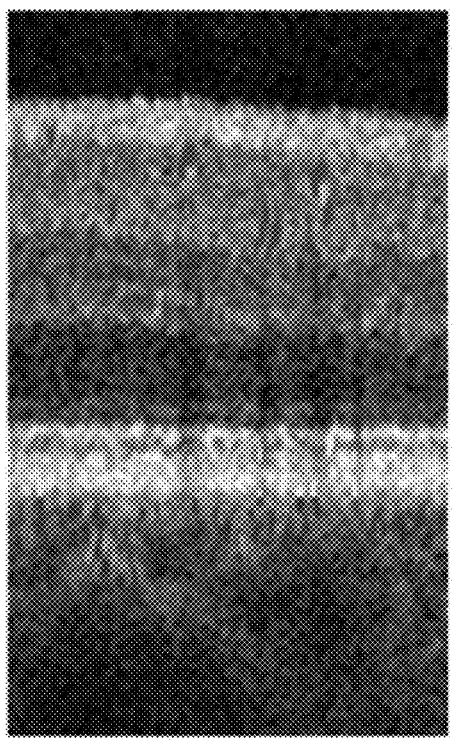

An example of shadowgraphic flow projection artifacts in a healthy retina cross section is shown in FIG. 1. For this figure the decorrelation signal (i.e., the OCT angiography data) is overlaid onto the OCT intensity signal (i.e., the structural OCT) to display a composite B-scan image, where the pixels 102, pixels 104, and pixels 106 correspond to inner retinal flow, outer retinal flow, and choroidal flow, respectively. In the healthy retina, there should be no vessels present in the outer retina. Thus, in the example image depicted in FIG. 1A, the pixels 104 located in the outer retina corresponds to shadowgraphic flow projections and do not reflect the presence of actual vascular structures. In FIG. 1B, the same cross section is shown with shadowgraphic projections removed using the PR method disclosed herein and described below. As depicted, the majority of blood flow indicated in the outer retina (e.g., pixels 108) has been removed. In addition, shadowgraphic flow projections in the inner retina (e.g., pixels 110) and choroid (e.g., pixels 112) are also substantially suppressed.

Susceptibility to shadowgraphic projection depends on signal intensity, which in turn is dependent on the reflectance of the tissue, as demonstrated in FIG. 1A. Specifically, in the retinal layers of the structural OCT scan having low intensity signals or low reflectance (i.e., the "darker" layers, such as inner nuclear layer (INL) and outer nuclear layer (ONL)) there are a greater number of projection artifacts present. Conversely, for retinal layers having high intensity signals or high reflectance (i.e., the "lighter" layers, such as the photoreceptor inner segment/outer segment IS/OS and retinal pigment epithelium (RPE)) there are a greater number of projection artifacts present. This dependence must be removed so that in situ flow may be better discriminated from flow projections. This can be achieved by normalizing decorrelation values from the OCT angiogram based on corresponding intensity values in the structural OCT. In an embodiment, this normalization may be performed by assuming that the projection is linear to the logarithm of the reflectance amplitude, log (I) and normalizing the decorrelation values D according to the following Equation (1):

$$A = \frac{D}{\log(I)} \quad (1)$$

Figure 2:
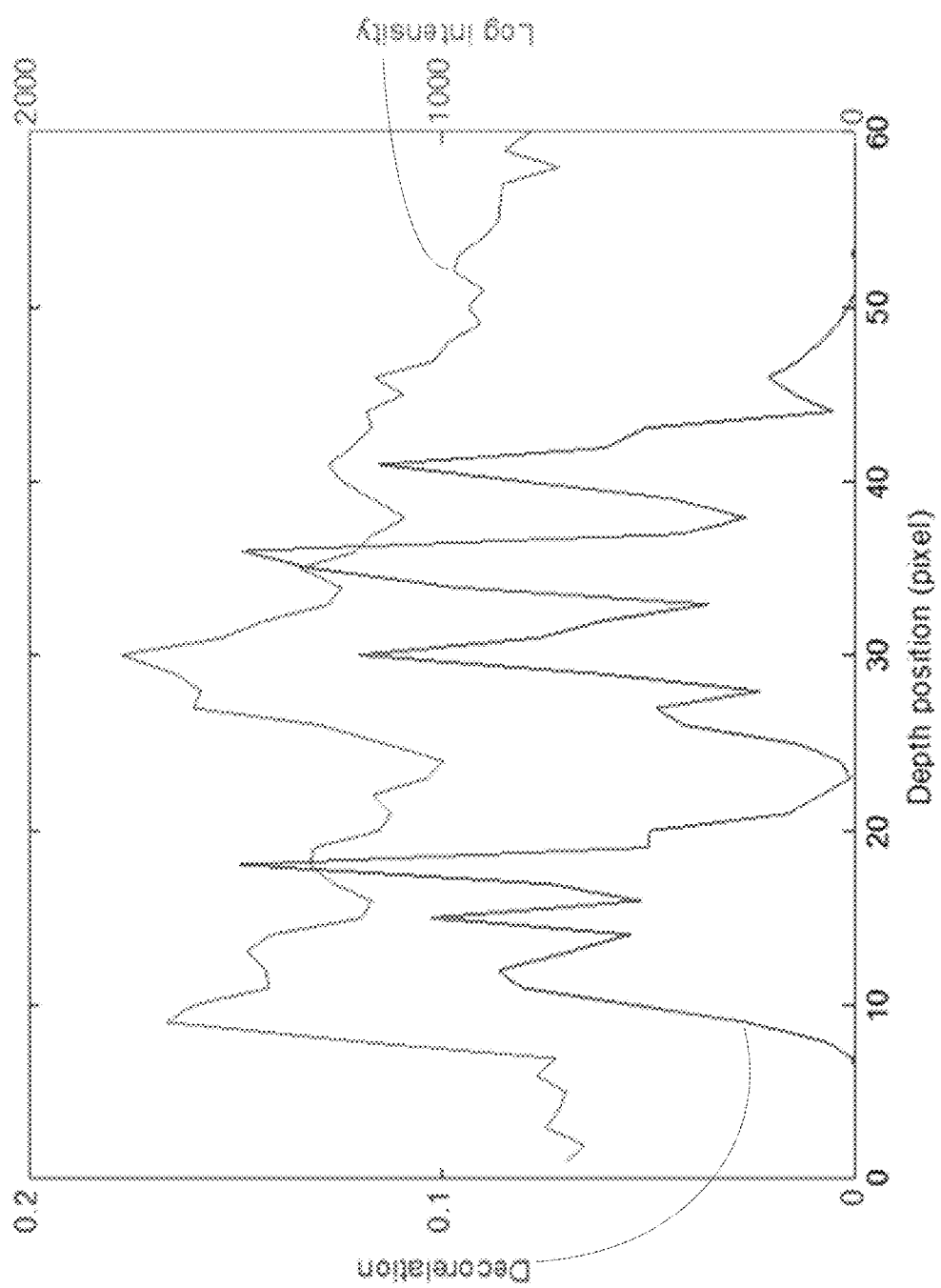
FIG. 2 shows an example of a decorrelation and log (intensity) signal values along a single A-scan as acquired by OCT. The x-axis indicates the pixel depth along the A-scan beginning at the most superficial depth and proceeding deeper into the retina.
Figure 3:
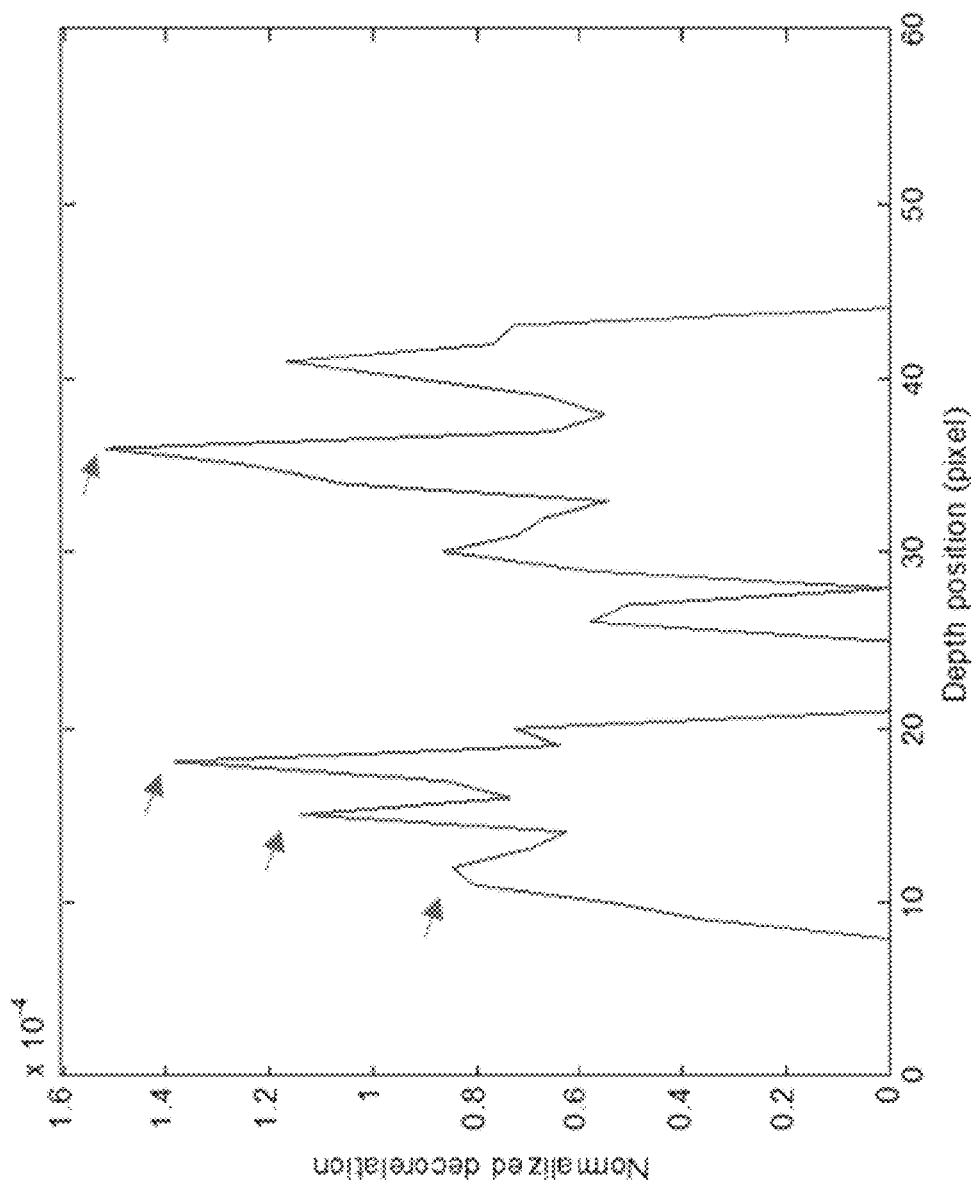
FIG. 3 shows an example of a normalized decorrelation signal along a single A-scan produced by application of Equation (1) (defined below) to the original decorrelation and intensity signals of FIG. 2. The arrows point to four successively higher peaks in the normalized decorrelation values.

An example axial scan (A-scan) of D and log(I) values is plotted in FIG. 2. After normalization of decorrelation values by Equation (1), the normalized decorrelation A values along the axial scan appear as in shown in FIG. 3. This figure illustrates that after the decorrelation values are adjusted to remove intensity dependency, several of the successive peaks along the axial scan become more pronounced (indicated by arrows in FIG. 3).

Figure 4:
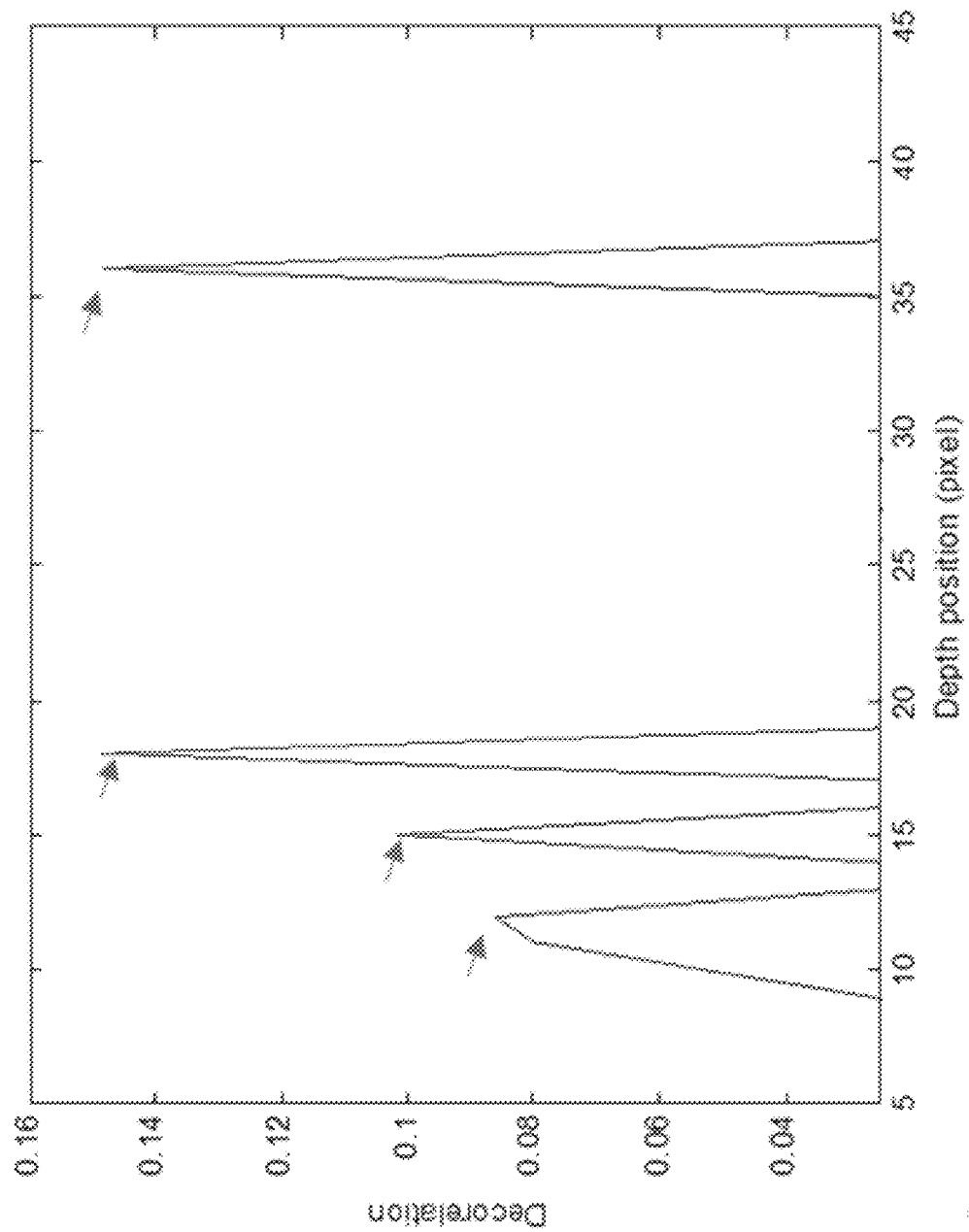
FIG. 4 shows an example of the original decorrelation values along a single A-scan after projection suppression according to the thresholding operation of Equation (2) (defined below). The arrows point to the four successively higher peaks identified in FIG. 3.

The basic idea of PR OCT-A is to resolve the ambiguity between in-situ flow in real blood vessels from projected flow signal. In an embodiment, this ambiguity is resolved by comparing the decorrelation value of a voxel with those of all voxels anterior to it, taking into account the effect of reflectance amplitude. Thus, the normalized decorrelation curve is used to identify the decorrelation peaks that are more likely to represent true in situ flow rather than projection artifacts. For this identification, it is assumed that a projected flow signal is weaker than the in-situ flow signal above it. By searching for successive higher peaks in A values along each axial scan from the shallow end (index i=1, e.g., the left of FIG. 3) to the deep end (increasing i, e.g. to right of FIG. 3), decorrelation peaks may be identified as being associated with real in-situ flow or rejected as projection artifacts. Hence, only those successively higher peaks are classified as flow and retained in the decorrelation signal; other values are suppressed as projection artifacts using a thresholding operation. In an embodiment, an exemplary classification and thresholding operation that identifies successively higher peaks along the A-scan and sets non-flow-classified voxels to zero (as depicted in FIG. 4) is as follows (also referred to as Equation (2)):

$$\begin{cases} C_n = D_n, & \text{if } A_n > (1+\alpha)\max(A_i), 1 \le i \le n-1 \\ C_n = 0, & \text{otherwise} \end{cases} \quad (2)$$

where i and n are the index of a voxel in an A-scan from the shallow (inner, proximal) end of the structural OCT dataset (e.g., corresponding to the shallow end of the sample), C is the normalized (PR-corrected) decorrelation values, and $\alpha$ is a factor included to account for noise in the structural OCT dataset ($\alpha$=0.1 for the examples disclosed herein). It is noted that a more sophisticated classification model based on experimental calibration and computational simulation may also be used to further improve the PR method.

Figures 5A, 5B, 5C:
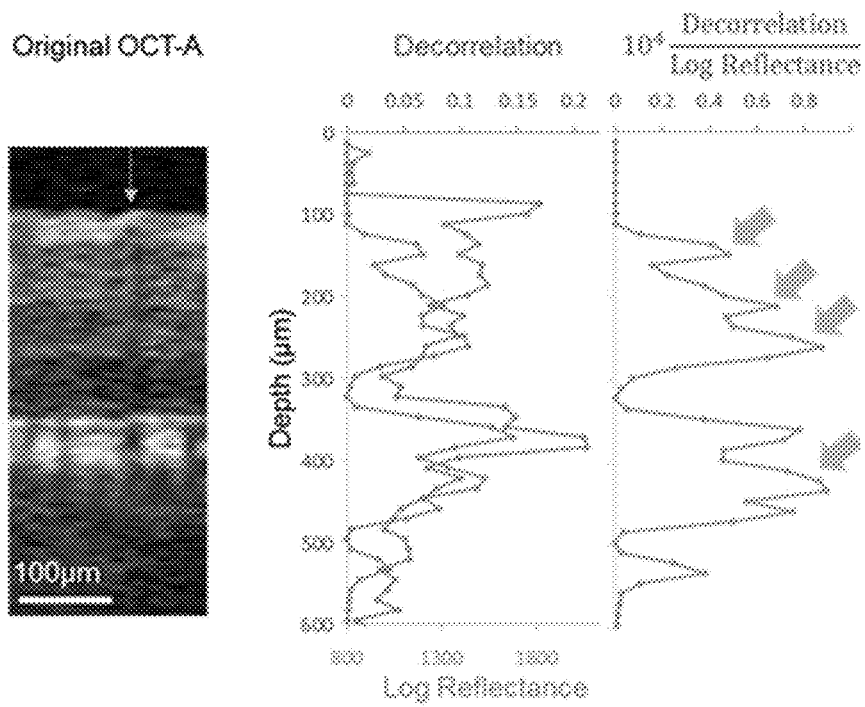
FIGS. 5A-5E show illustrations of projection resolved (PR) optical coherence tomography angiography (OCT-A).
Figures 5D, 5E:
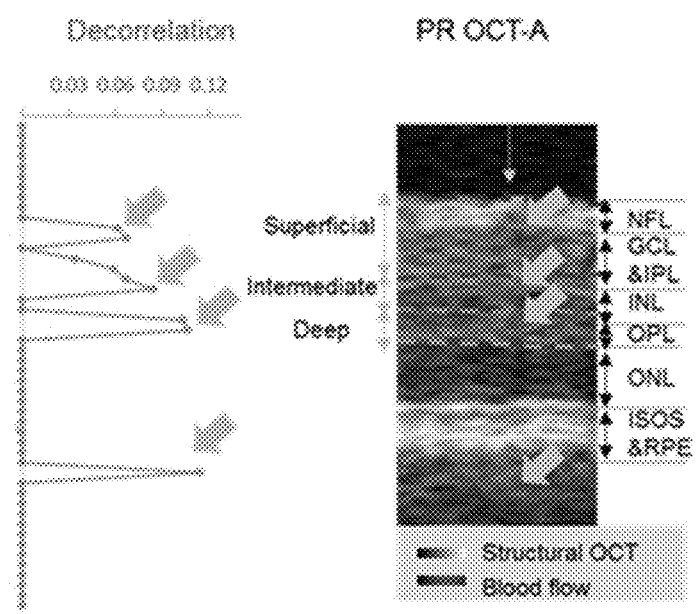

An illustration of the full shadowgraphic flow projection procedure as described above is shown in FIGS. 5A-5E. The original composite cross sectional B-scan in FIG. 5A shows pronounced shadowgraphic flow projection artifacts prior to PR OCT-A processing to suppress them. FIG. 5B shows the associated original decorrelation and intensity values along the A-scan line indicated by the arrow 502 in FIG. 5A. As discussed herein, the decorrelation values along the A-scan may be normalized according to Equation (1). FIG. 5C shows the normalized decorrelation values along the A-scan, and four successively increasing peaks (denoted as 504, 506, 508, and 510) are identified as the qualified A values, and corresponding original decorrelation values D are kept as C according to the thresholding Equation (2). The original decorrelation signal following the threshold operation is plotted in FIG. 5D. FIG. 5E shows an overlay of the resulting projection-suppressed decorrelation on the OCT reflectance intensity. Following the projection suppression procedure (i.e., after removal of signal values assumed to be projection artifact) remaining signals are unmodified and kept at their original decorrelation signal values. As shown in FIG. 5E, the PR algorithm effectively removes tail artifacts from retinal vessels and recovers accurate information on their axial position (FIG. 1). Furthermore, the resulting cross-sectional angiograms in the macular region reveal 3 distinct vascular plexuses in the inner retina.

EXAMPLES

The following examples are illustrative of the disclosed method. In light of this disclosure, those skilled in the art will recognize that variations of these examples and other examples of the disclosed method would be possible without undue experimentation.

OCT Angiography Data Acquisition

In the following examples, OCT angiography data was acquired using a commercial spectral domain OCT instrument (RTVue-XR Avanti; Optovue, Inc., Fremont, Calif.) that has a center wavelength of 840 nm with a full-width half-maximum bandwidth of 45 nm and an axial scan rate of 70 kHz. Angiography scans were performed using the resident AngioVue software. The 3D volumetric scans consisted of a 3×3 mm area with a 1.6 mm depth (304×304×512 pixels). In the fast transverse scanning direction, 304 A-scans were sampled. Two repeated B-scans were captured at a fixed position before proceeding to the next location. A total of 304 locations along a 3 mm distance in the slow transverse direction were sampled to form a 3D data cube. All 608 B-scans in each data cube were acquired in 2.9 seconds. Two volumetric raster scans, one x-fast scan and one y-fast scan, were acquired, registered, and merged into one 3D angiogram (Kraus M et al, Biomed Opt Express 3, 1182-1189 (2012); incorporated by reference herein). Blood flow is detected using the AngioVue software, a commercial version of the split-spectrum amplitude-decorrelation angiography (SSADA) algorithm (Liu L et al, JAMA Ophthalmology 133, 1045-1052 (2015); incorporated by reference herein). The SSADA algorithm calculates the signal amplitude-decorrelation between two consecutive B-scans of the same location. The SSADA algorithm split the OCT spectrum to obtain multiple B-frame images from each B-scan. The split B-frames have longer axial coherence gate, which reduces noise from axial bulk motion. Because the spectral splits are associated with independent speckle patterns, they provide independent flow signal from their respective speckle decorrelation images. Averaging the decorrelation signals from the spectral splits enhances the signal-to-noise ratio of flow detection by up to 4-fold (Jia Y et al, Opt Express 20, 4710-4725 (2012); Gao S et al, Opt Letters 40, 2305-2308 (2015); incorporated by reference herein).

The volume data were segmented using directional graph search (Zhang M et al, Biomed Opt Express 6, 4661-4675 (2015); incorporated by reference herein), which gives reference boundaries separating the ILM, boundary of the IPL, INL, OPL, ONL, photoreceptor IS/OS junction, RPE, and Bruch's membrane (BM). En face angiograms are constructed by maximum flow projection within slabs that are defined by the segmented boundaries. The inner retinal slab include layers between the ILM and OPL, and the outer retinal slab includes layers between the ONL and BM. Color composite en face OCT angiograms are generated using the top-view maximum intensity projection technique (Wang R et al, 2007, supra; Makita F et al, 2011, supra; Jia Y et al, 2012, supra; Wallis J et al, Med Imaging IEEE Trans 8, 297-230 (1989); incorporated by reference herein) with the more superficial (inner, proximal) slab is placed on top of deeper slabs, thus providing 3D information on a 2D display (Jia Y et al, 2012, supra; incorporated by reference herein).

Study Population

In the following examples, PR was systematically tested in 13 healthy participants (one eye each) whose ages ranged from 25 to 58 years. One participant with neovascular age-related macular degeneration confirmed by clinical examination and fluorescein angiography was also used to demonstrate the visualization of choroidal neovascularization (CNV). Institutional approval for human subject research was obtained.

Enhancement of Depth Resolution to Reveal 3 Retinal Plexuses

Figure 6A:
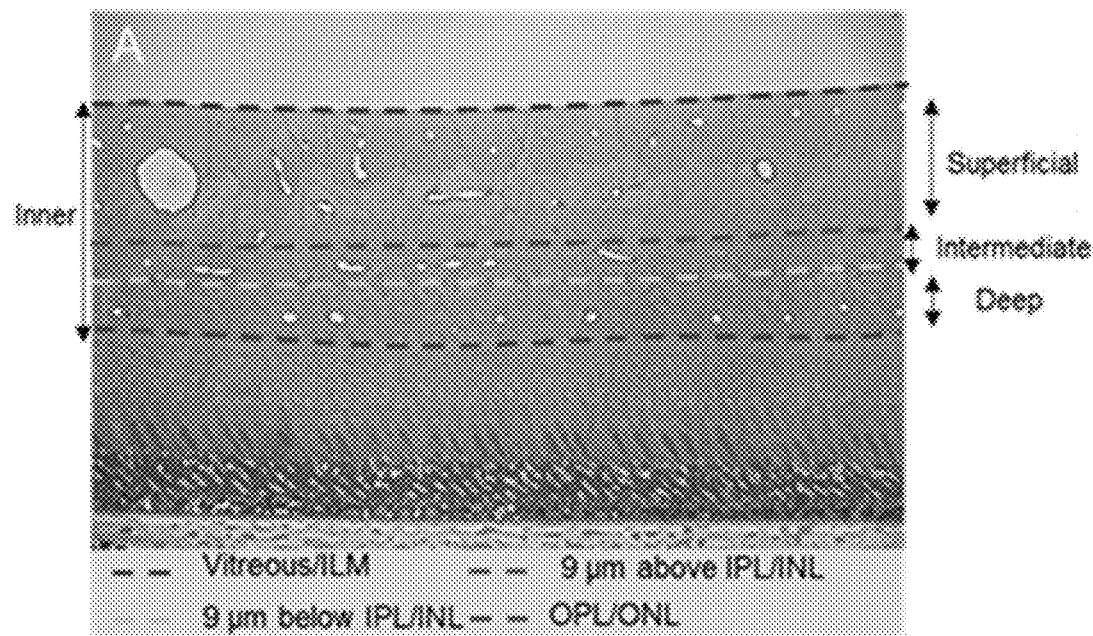
FIGS. 6A and 6B show a cross sectional images of the retina obtained by histology and a corresponding cross section image obtained by OCT angiography using the disclosed method.
Figure 6B:
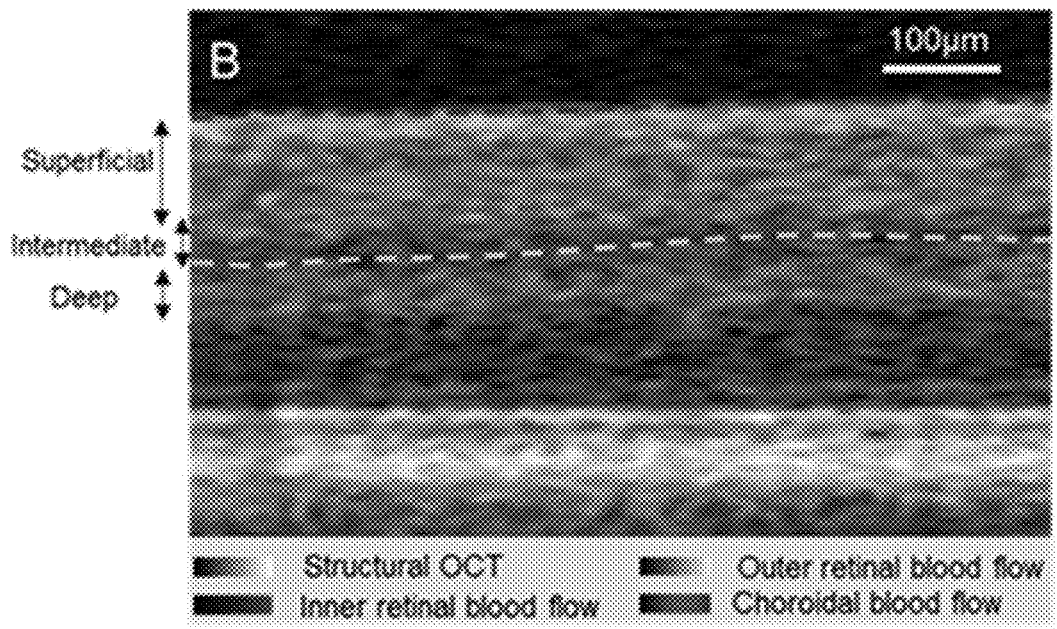

In clinical OCT-A, the retinal circulation is dominated by the superficial layer and the deeper vascular layers have been difficult to visualize as distinct plexuses. Previous histological studies have shown that there are three vascular plexuses in human macula (except in the immediate peripapillary region where there are four). FIGS. 6A and 6B illustrate the delineation between these layers for the non-human primate retina in histologic cross sectional image and a composite B-scan OCT angiography image, respectively. The superficial retinal vascular plexus is in the nerve fiber layer (NFL), ganglion cell layer (GCL), and the superficial portion of the IPL. The intermediate capillary plexus is located at the junction between the IPL and the INL. The deep capillary plexus is located at the junction between the INL and the OPL. These 3 plexuses have been well characterized histologically in non-human primates and recently in human cadaveric eyes (Snodderly D et al, *J Compar Neur* 297, 145-163 (1990); Snodderly D et al, *J Neurosci* 12, 1169-1193 (1992); Gariano R et al, *Invest Ophthalmol Vis Sci* 35, 3442-3455 (1994); Chan G et al, *Invest Ophthalmol Vis Sci* 53, 5502-5514 (2012); P Tan et al, *Invest Ophthalmol Vis Sci* 53, 5728-5736 (2012); incorporated by reference herein). However, clinical imaging with FA is unable to resolve the 3 plexuses due to inherent lack of depth resolution in the method, and early attempts at visualization using OCT angiography were limited due to projection artifacts from the superficial inner retinal layer. Using the PR method disclosed herein to suppress these artifacts, in vivo visualization of the superficial, intermediate, and deep inner retinal layers as unique vascular plexuses is achieved. As shown in FIG. 6B, the images obtained by OCT angiography using the disclosed method are comparable to those obtained by histology.

A comparison of depth-resolved OCT-A was performed without projection suppression and with projection suppression, using 2 different methods. For the purpose of OCT image segmentation, the automated image processing software was set to define the intermediate plexuses as the slab 25 µm above to 25 µm below the IPL/INL boundary. The deep plexus ends at the deep boundary of the OPL. The outer retinal slab was defined as including ONL, photoreceptor layer, the RPE, and ending at the BM. En face OCT angiograms were obtained using maximum flow projection within these segmented slabs.

While OCT has good depth resolution, this resolution was degraded in OCT-A by the projection artifact, which cause images of deeper slabs to be dominated by projected flow. On the cross-sectional angiogram (FIG. 7), this means the superficial retinal vessels have long tails that streak vertically down all the retinal layers and even into the choroid. On the en face angiograms of the deeper plexuses and the outer retina (FIG. 7), the projected flow from the superficial plexus predominates, making the capillary plexuses difficult to recognize and cluttering the normally avascular outer retinal slab.

In a slab-subtraction (SS) method, the maximum projected flow from the more superficial slab is subtracted from the current slab. The SS algorithm was implemented using Equation 3 below:

$$C_{slab2} = \begin{cases} D_{slab2} - D_{slab1}, & \text{if } D_{slab2} > D_{slab1} \\ 0, & \text{otherwise} \end{cases} \quad (3)$$

where $D_{slab2}$ is the decorrelation value from maximum flow projection within the slab of interest, $D_{slab1}$ is the maximum flow projection of all layers above $D_{slab2}$, and $C_{slab2}$ is the resulting decorrelation value of the SS OCT-A.

The SS algorithm effectively removed most projection artifacts from the deeper plexuses and the outer retinal, but unfortunately left shadowing artifacts in its place. This meant the capillaries in the intermediate and deep plexuses (FIG. 7, middle column) become severely fragmented and no longer recognizable as continuous networks. The SS OCT-A images also appear dimmer because subtraction lowered the decorrelation values. The SS algorithm cannot be applied to cross-sectional images, so the projection on cross-sectional images remains the same.

Using PR, the distinct vascular patterns in the 3 retinal plexuses may now be visualized (FIG. 7, right column). These cross-sectional angiograms show vessels without tails, so that their axial locations can be pinpointed. There are concentrations of vessels at the level of the intermediate and deep plexuses. The projection artifacts in the outer retina are largely eliminated, but scattered residual artifacts remain at the level of the RPE. The en face angiograms show that the superficial plexus contains both large and small vessels in a centripetal branching pattern that ends at the foveal circle. The intermediate and deep plexuses are purely composed of capillaries in maze-like networks. Although these 2 plexuses have similar texture, their patterns are not the same when examined in detail. In the deep plexus, there is still some shadowing under the largest vessels from the superficial plexus. Thus the PR algorithm does not perfectly preserve vascular continuity there. However, the improvement over SS is dramatic.

Another advantage of the PR algorithm is that it produces a truly 3D OCT-A, so that projection-suppressed C-scan images (i.e., individual image slices viewed in the axial direction, with no en face projection) may be observed. An example of such a projection-suppressed image, taken from a screenshot of a "fly through" video, is shown in FIG. 8. The fly through video shows that without projection suppression, the superficial vascular pattern is duplicated several times as one flies through deeper reflective layers. In contrast, PR OCT-A shows the distinct patterns characteristic of the various retinal and choroidal plexuses. At this depth in the image stack depicted in FIG. 8, there are no large vessels, as FIG. 8B depicts the structural shadows which exist behind large vessels. Clearly, projections from the more superficial large vessels that appear in FIG. 8A have not been projected in FIG. 8B.

Figure 9A:
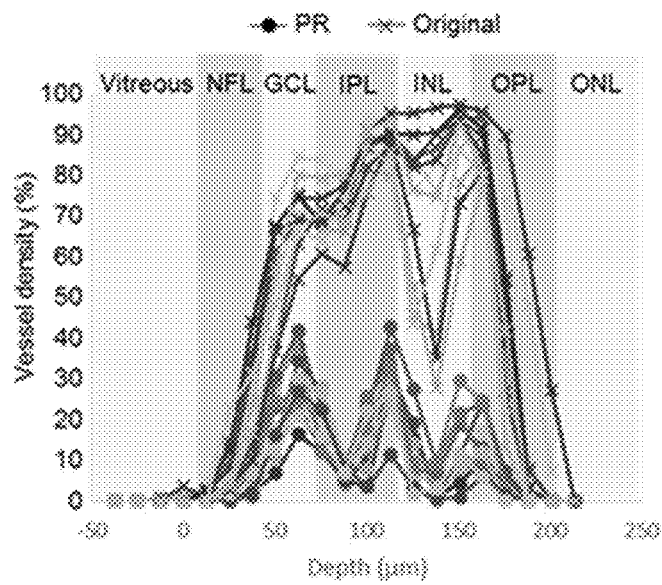
FIGS. 9A and 9B show plots of retinal vessel density as a function of depth computed from OCT-A with and without projection removal using the PR algorithm. The ROI in a 3×0.1 millimeter (mm) temporal perifoveal location was defined in FIG. 7A1 (rectangle 704).
Figure 9B:
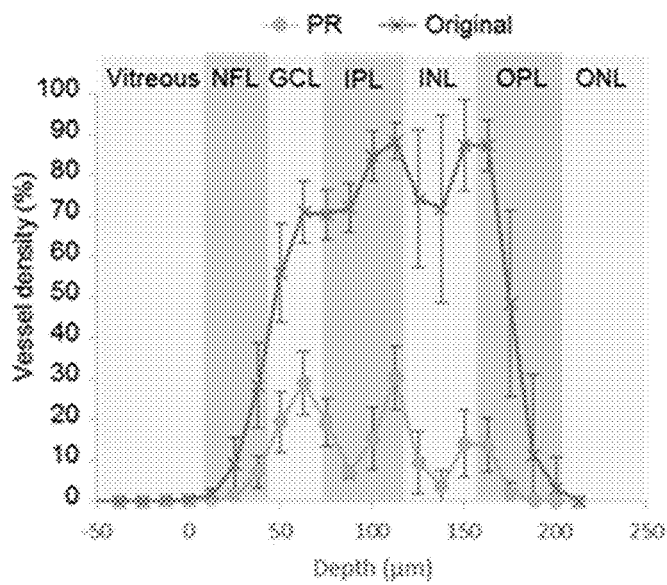

To quantitatively demonstrate that 3 retinal plexuses could be observed in PR OCT-A, all A-scan lines from the 13 healthy eyes at the segmented IPL/INL boundary were registered within a 3×0.1 mm region of interest (ROI) in the temporal perifoveal area defined by the narrow rectangle in FIG. 7B1. The vessel densities were calculated as a function of depth in 12.5 µm increments (FIG. 9). Without projection suppression, the vessel density appeared to reach higher plateaus at the IPL and OPL, presumably due to accumulation of projected flow in the relatively high reflectance plexiform layers. But there were no clear peaks. In contrast, the PR OCT-A showed 3 sharp peaks of vessel density corresponding to the 3 retinal vascular plexuses (FIG. 9): the superficial plexus peaks within the GCL, the intermediate plexus peaks at the IPL/INL junction with valleys 25 µm on each side, and the deep plexus peaks at the INL/OPL junction which terminated before reaching the ONL. This pattern was present in all 13 study participants.

Vascular Pattern Similarity as a Measure of Projection Artifact Suppression

Without projection suppression, the vascular pattern in in overlying layers is duplicated in all deeper angiogram slabs. Thus en face OCT-A in deeper slabs would all appear to have patterns similar to the slabs above them. Successful projection suppression should reduce this similarity as much as possible. To evaluate the performance of projection suppression, the Pearson's product-moment correlation coefficient is used to quantify the similarity between vascular patterns in the deeper en face OCT-A slabs in comparison to the vascular pattern in the aggregate slab of all layers above. The Pearson correlation coefficient r is calculated according to Equation 4 as:

$$r = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \quad (4)$$

where i is the index of pixels within the angiogram, $n=304^2$ is the total number of pixels in the angiogram, x represent the decorrelation values of the deeper slab obtained by maximum flow projection, and y represent the decorrelation values of the more superficial slab containing all layers above. $\bar{x}$ and $\bar{y}$ represent the respective slab averages, with $\bar{x}$ calculated as:

$$\bar{x} = \frac{1}{n}\sum_{i=1}^{n} x_i \quad (5)$$

and analogously for $\bar{y}$. Pearson's r takes value between −1 and 1. A r value close to 1 represents strong positive correlation (similarity), 0 represents no correlation, and values close to −1 represents negative correlation. Note that the Pearson's correlation coefficient is insensitive to brightness and contrast variation or manipulations.

Figure 10:
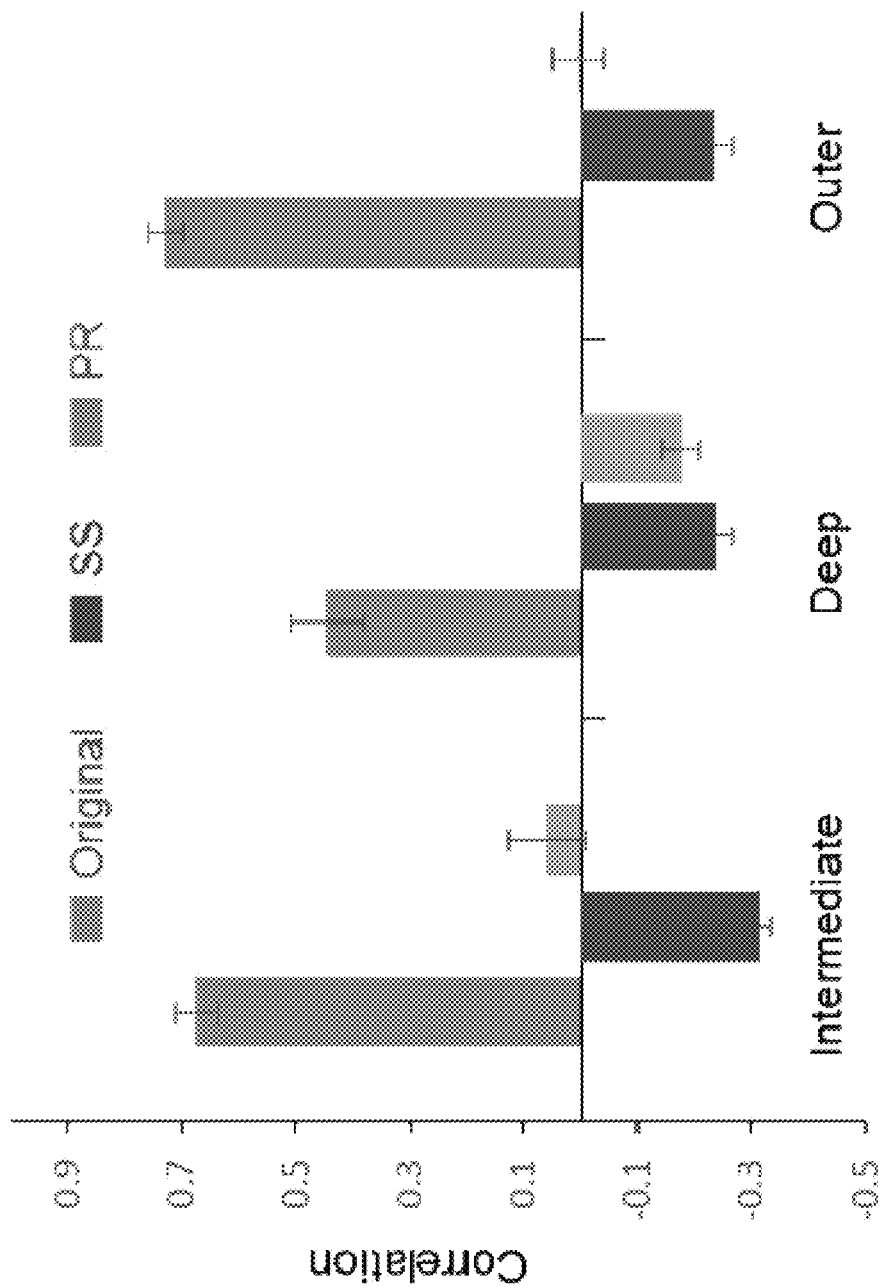
FIG. 10 shows correlation results for the en face angiogram of the deeper slabs—intermediate plexus, deep plexus, and outer retina—relative to all the layers above them. The differences between the original, SS, and PR OCT-A were statistically significant for all 3 slabs ($p<0.00000001$ by paired t tests.).

This method was applied to OCT-A from the 13 healthy participants (FIG. 10). Correlation for the intermediate plexus slab was calculated relative to the superficial plexus. Correlation for the deep plexus was calculated relative to the aggregate slab containing both the superficial and intermediate plexus. And correlation for the outer retinal slab was calculated relative to the aggregate slab containing all 3 plexus in the inner retina.

Without projection suppression, r was greater than 0.55 for all 3 deeper slabs, indicating strong projection artifacts. The standard SS algorithm produced negative r between −0.2 and −0.3, which must be due to the fact that it produced shadows where there were overlying flow signal. The novel PR algorithm successfully suppressed projection in all 3 deeper layers so that r was less than 0.1.

Preservation of Vascular Continuity

Figure 11:
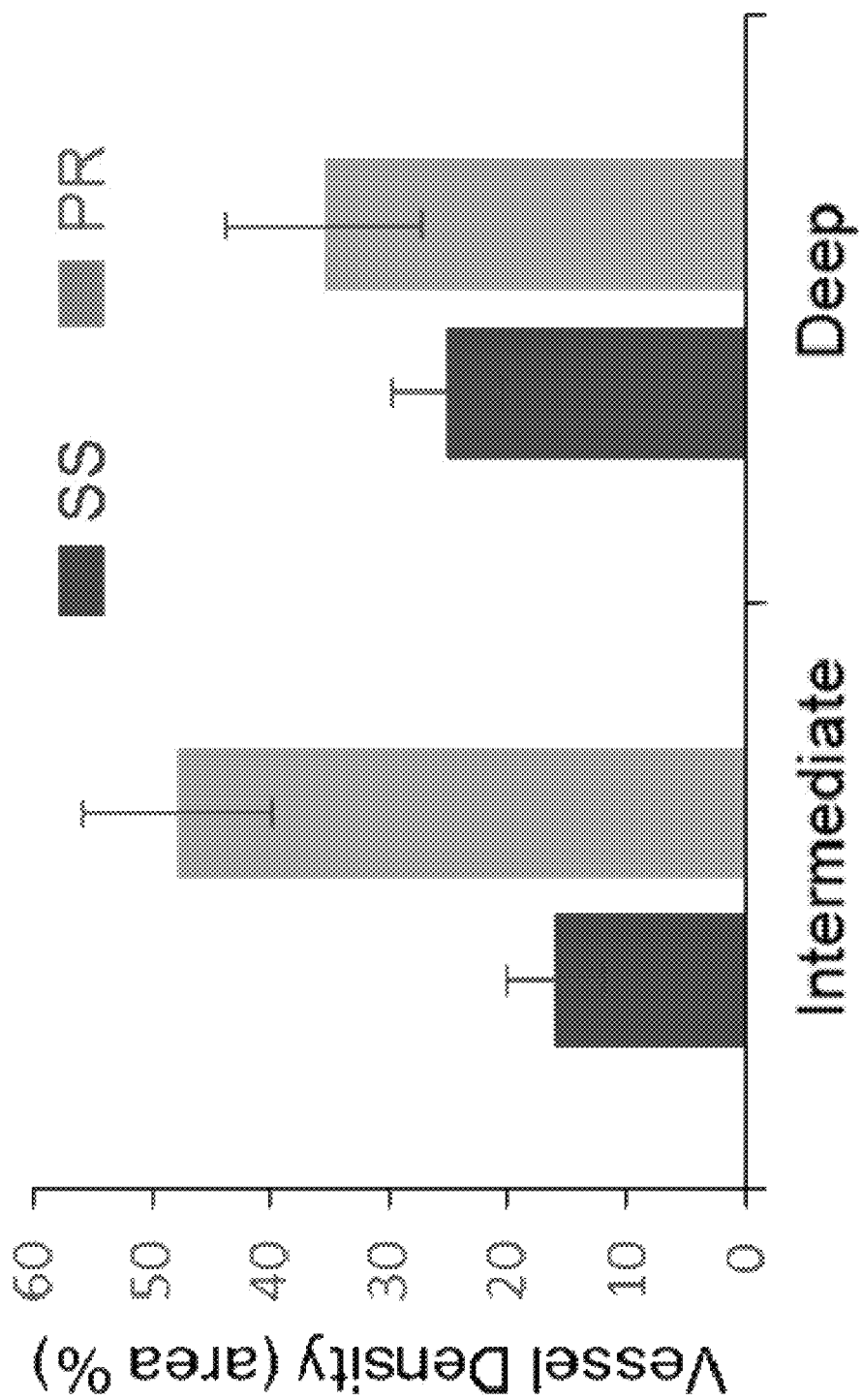
FIG. 11 shows a comparison of parafoveal vessel density of the intermediate and deep capillary plexuses obtained using SS and PR algorithms. The differences between the 2 algorithms were statistically significant for both plexuses ($p<0.000001$, paired t-test).

A successful projection suppression algorithm should remove as much projection artifact as possible, but should also preserve as much in-situ flow signal (real vessels) as possible. To quantify the preservation of flow signal, the retinal vessel density of parafoveal area (annulus between the blue and green circles in FIG. 7B1). The vessel density was calculated using a simple noise threshold, suprathreshold pixels on the en face angiograms are counted as vessel pixels and the rest as static pixels. The background decorrelation noise was calculated from the retinal angiogram in the foveal avascular zone (inside blue circle in FIG. 7B1). The threshold was set at noise mean+2.33 standard deviations (99 percentile cut-point assuming normal distribution). According the vessel density metric (FIG. 11), the PR algorithm preserved flow signal significantly better than the SS algorithm. This confirmed the qualitative impression from the inspection of the en face angiograms (FIG. 7), which showed that the standard SS algorithm fragmented the capillary networks of the intermediate and deep plexuses, while the PR algorithm was able to largely preserve the continuity of the capillary plexuses.

Figure 12:
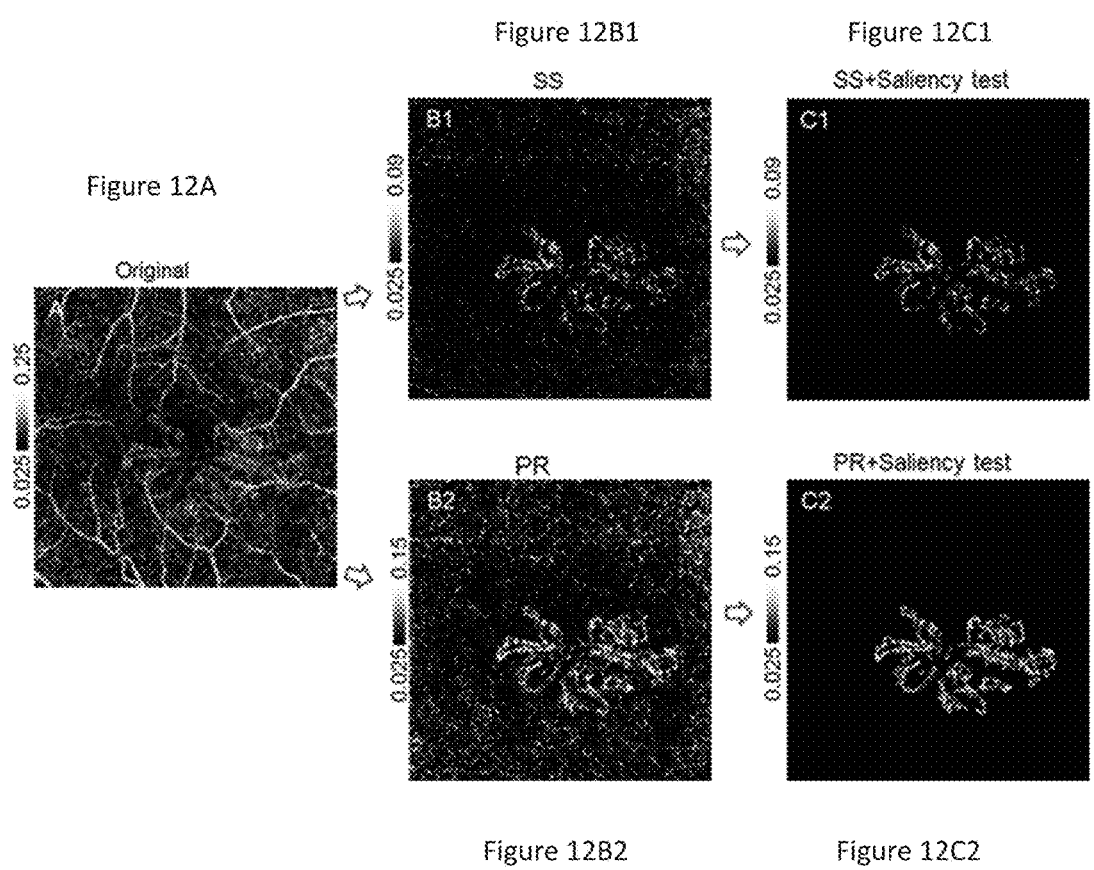

The preservation of vascular integrity is even more important in the visualization of pathologies such as CNV, an abnormal growth of new vessels in the normally avascular outer retinal slab. Strong projection artifacts in the RPE layer make the detection of CNV more difficult by introducing a dense background clutter (FIG. 12A). Applying either SS or PR algorithm removes much of the artefactual flow signal and makes the CNV stand out better (FIG. 12). An additional Saliency-based algorithm is further needed to completely remove the background clutter by recognizing its scattered and disconnected texture (Liu L, et al, 2015; supra). The SS+Saliency algorithm was able to recover the CNV network, but the vascular loops are severely fragmented (FIG. 12C1). The PR+Saliency algorithm recovered a more continuous CNV with minimal gaps in the network (FIG. 12C2). Clean and complete detection of CNV is important for quantification of the CNV vessel area, an important parameter in assessing the effectiveness of antevascular endothelial grow factor (VEGF) therapy and the monitoring of recurrent growth that may prompt additional treatment.

OCT Angiography Image Processing System

Figure 13:
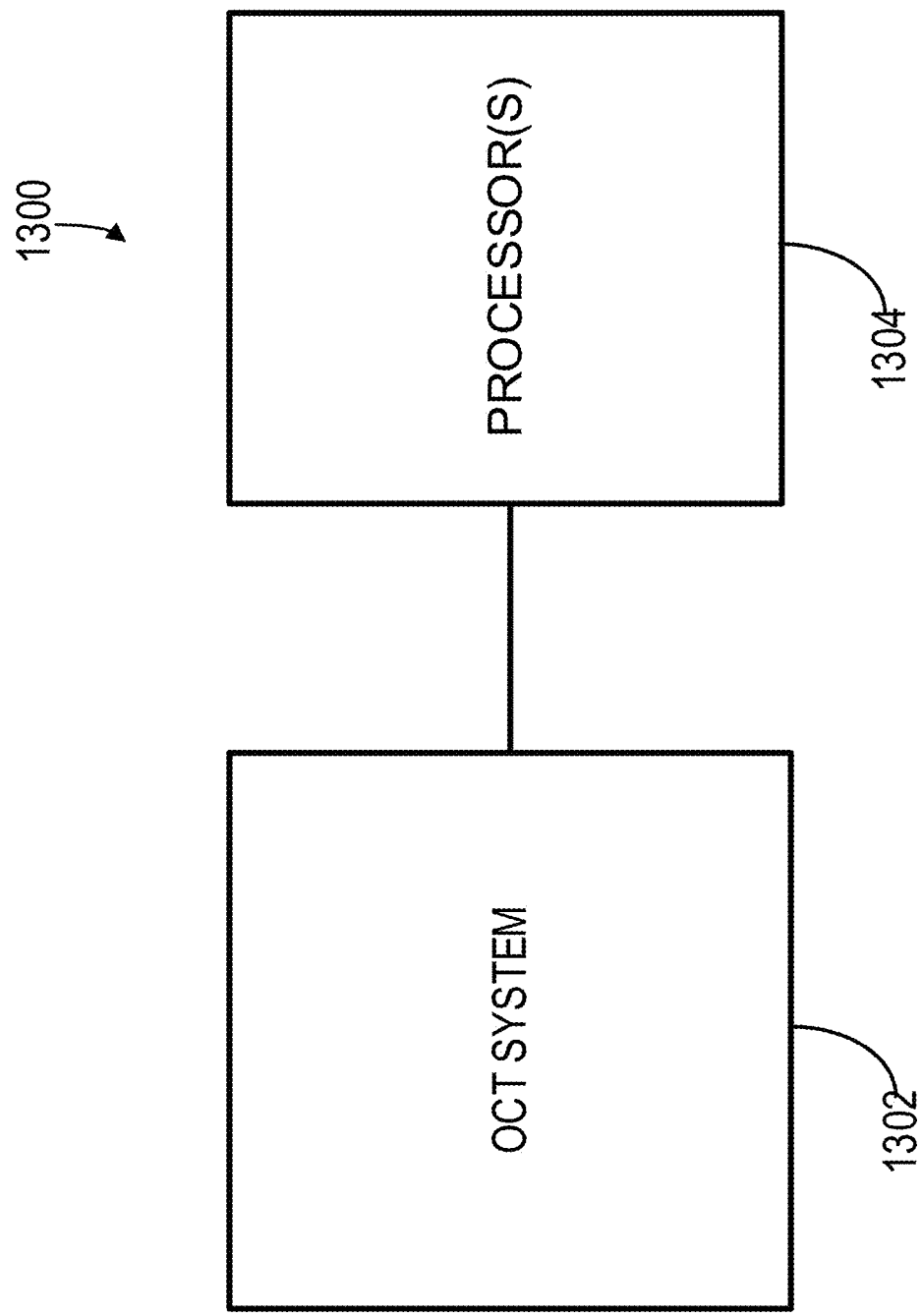
FIG. 13 schematically shows an example system processing OCT datasets to suppress shadowgraphic flow projections in OCT angiography datasets in accordance with the disclosure.

FIG. 13 schematically shows an example system 1300 for OCT angiography image processing in accordance with various embodiments. System 1300 comprises an OCT system 1302 configured to acquire an OCT image comprising OCT interferograms and one or more processors or computing systems 1304 that are configured to implement the various processing routines described herein. OCT system 1302 may comprise an OCT system suitable for OCT angiography applications, e.g., a swept source OCT system. For example, the OCT system 1302 may include all or selected aspects of the system 1600 shown in FIG. 16. In some embodiments, the processor(s) 1304 shown in FIG. 13 may correspond to the computer 1620 shown in FIG. 16.

In various embodiments, an OCT system may be adapted to allow an operator to perform various tasks. For example, an OCT system may be adapted to allow an operator to configure and/or launch various ones of the herein described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

In some embodiments, the above described methods and processes may be tied to a computing system, including one or more computers. In particular, the methods and processes described herein, e.g., method 1500 described below, may be implemented as a computer application, computer service, computer API, computer library, and/or other computer program product.

Figure 14:
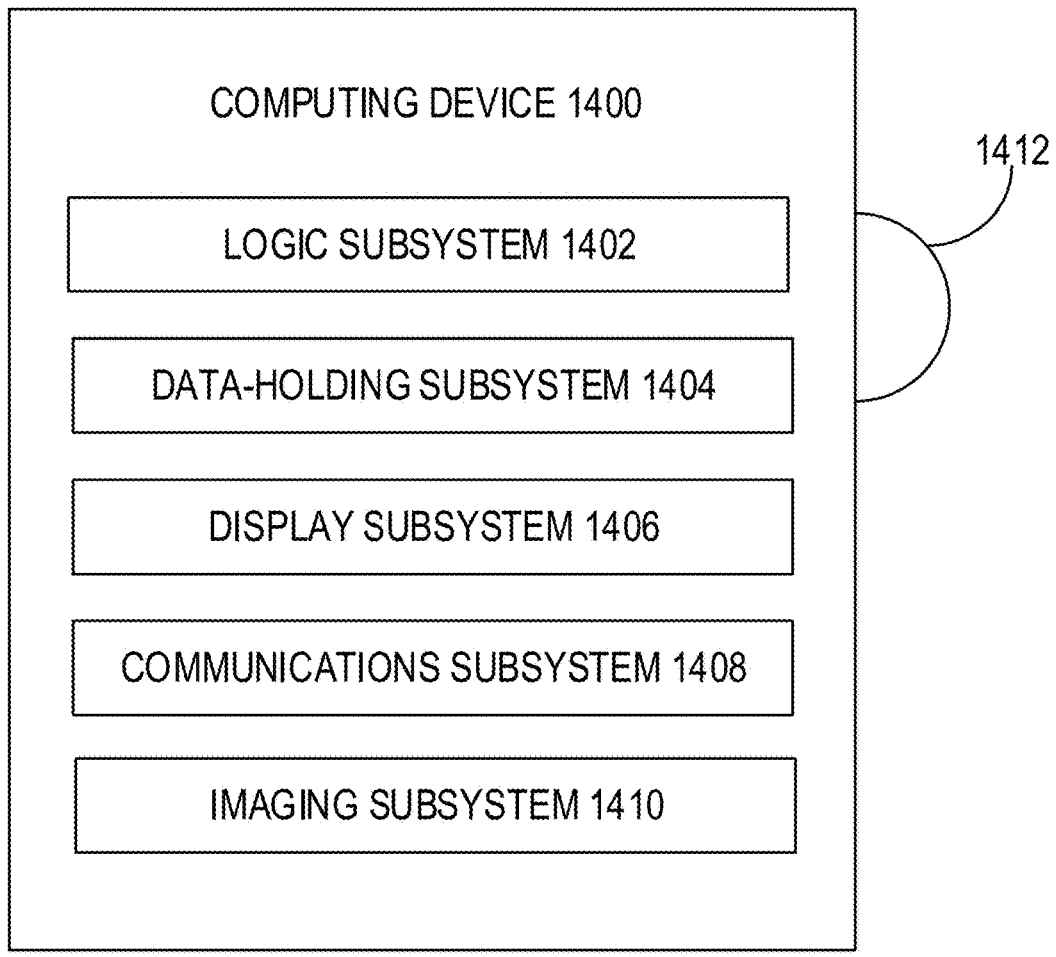
FIG. 14 schematically shows an example of a computing system in accordance with the disclosure.

FIG. 14 schematically shows a non-limiting computing device 1400 that may perform one or more of the above described methods and processes. For example, computing device 1400 may represent a processor 1304 included in system 1300 described above, and may be operatively coupled to, in communication with, or included in an OCT system (e.g., OCT image acquisition apparatus). Computing device 1400 is shown in simplified form. It is to be understood that virtually any computer architecture may be used without departing from the scope of this disclosure. In different embodiments, computing device 1400 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1400 includes a logic subsystem 1402 and a data-holding subsystem 1404. Computing device 1400 may optionally include a display subsystem 1406, a communication subsystem 1408, an imaging subsystem 1410, and/or other components not shown in FIG. 14. Computing device 1400 may also optionally include user input devices such as manually actuated buttons, switches, keyboards, mice, game controllers, cameras, microphones, and/or touch screens, for example.

Logic subsystem 1402 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1404 may include one or more physical, non-transitory, devices configured to hold data and/or instructions executable by the logic subsystem to implement the herein described methods and processes. When such methods and processes are implemented, the state of data-holding subsystem 1404 may be transformed (e.g., to hold different data).

Data-holding subsystem 1404 may include removable media and/or built-in devices. Data-holding subsystem 1404 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1404 may include devices with one or more of the following characteristics: volatile, nonvolatile, dynamic, static, read/write, read-only, random access, sequential access, location addressable, file addressable, and content addressable. In some embodiments, logic subsystem 1402 and data-holding subsystem 1404 may be integrated into one or more common devices, such as an application specific integrated circuit or a system on a chip.

FIG. 14 also shows an aspect of the data-holding subsystem in the form of removable computer-readable storage media 1412, which may be used to store and/or transfer data and/or instructions executable to implement the herein described methods and processes. Removable computer-readable storage media 1412 may take the form of CDs, DVDs, HD-DVDs, Blu-Ray Discs, EEPROMs, flash memory cards, USB storage devices, and/or floppy disks, among others.

When included, display subsystem 1406 may be used to present a visual representation of data held by data-holding subsystem 1404. As the herein described methods and processes change the data held by the data-holding subsystem, and thus transform the state of the data-holding subsystem, the state of display subsystem 1406 may likewise be transformed to visually represent changes in the underlying data. Display subsystem 1406 may include one or more display devices utilizing virtually any type of technology. Such display devices may be combined with logic subsystem 1402 and/or data-holding subsystem 1404 in a shared enclosure, or such display devices may be peripheral display devices.

When included, communication subsystem 1408 may be configured to communicatively couple computing device 1400 with one or more other computing devices. Communication subsystem 1408 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1400 to send and/or receive messages to and/or from other devices via a network such as the Internet.

When included, imaging subsystem 1410 may be used acquire and/or process any suitable image data from various sensors or imaging devices in communication with computing device 1400. For example, imaging subsystem 1410 may be configured to acquire OCT image data, e.g., interferograms, as part of an OCT system, e.g., OCT system 1302 described above. Imaging subsystem 1410 may be combined with logic subsystem 1402 and/or data-holding subsystem 1404 in a shared enclosure, or such imaging subsystems may comprise periphery imaging devices. Data received from the imaging subsystem may be held by data-holding subsystem 1404 and/or removable computer-readable storage media 1412, for example.

Figure 15:
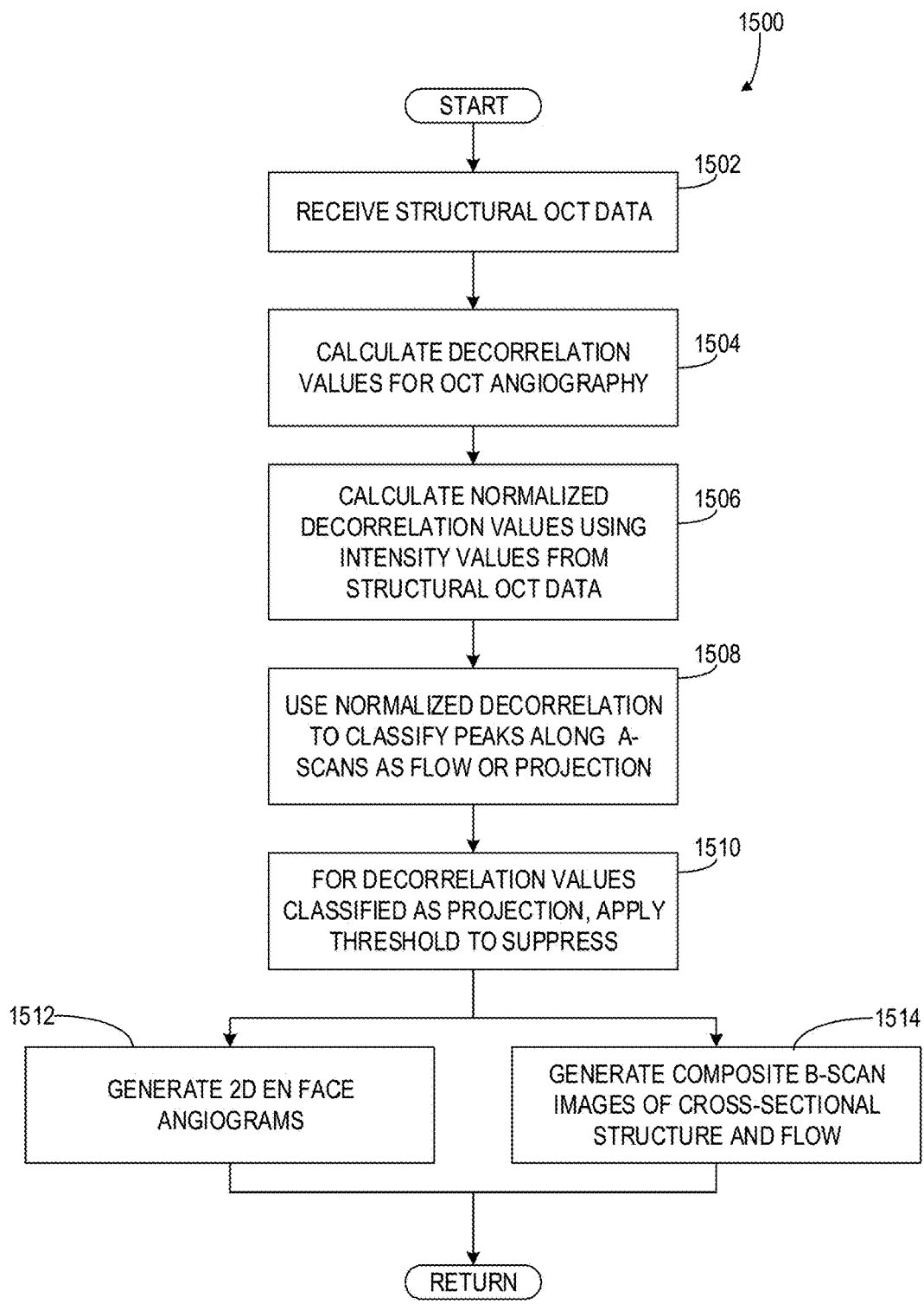
FIG. 15 shows an example of a method for processing OCT angiography datasets to suppress shadowgraphic flow projections in accordance with the disclosure.

FIG. 15 shows an example method 1500 for processing a set of B-scans to suppress shadowgraphic flow projections in accordance with various embodiments. Method 1500 may be implemented by a system such as system 1300 described above, that includes an OCT system and one or more processors or computing systems, such as computing device 1400 described above. For example, one or more operations described herein may be implemented by one or more processors having physical circuitry programmed to perform the operations. In embodiments, one or more steps of method 1500 may be automatically performed by one or more processors or computing devices. Further, various acts illustrated in FIG. 15 may be performed in the sequence illustrated, in other sequences, in parallel, or in some cases omitted. Method 1500 may be used to generate shadow-graphic flow-suppressed OCT angiography data for presentation as 2D en face angiograms or as cross-sectional composite B-scan images.

At 1502, method 1500 includes receiving structural OCT data in the form of one or more B-scans, each B-scan being comprised of one or more A-scans. For example, OCT scan data including a plurality of interferograms may be acquired from a swept-source or other OCT system, e.g., the system 1300 shown in FIG. 13. In other embodiments, the OCT data may be received by a computing device from an OCT scanning system via a network or from a storage medium coupled to or in communication with the computing device.

At 1504, method 1500 includes application of an OCT angiography algorithm to calculate the decorrelation values associated with the received structural OCT data. This calculation of decorrelation values may be performed using any suitable OCT angiography algorithm, for example, the SSADA algorithm (Jia Y et al, 2012 supra; Gao S et al, 2015 supra). At 1506, these decorrelation values are used along with intensity valued to calculate normalized decorrelation values for subsequent processing. In an embodiment, these normalized decorrelation values may be calculated using Equation (1).

At 1508, method 1500 begins to serially process the normalized decorrelation values associated with each A-scan of the structural OCT dataset. In an embodiment, each A-scan is processed in the proximal (shallow) to distal (deep) direction of the axial scan direction to identify successively larger peak normalized decorrelation values. The identified peaks are classified as flow signals, while the non-peak values are classified as projection artifact (i.e., non-flow signals). At 1510, for normalized decorrelation values determined to be projection artifacts in 1508, the corresponding (un-normalized) decorrelation signals are suppressed using a threshold operation. In one embodiment, the classification 1508 and suppression 1510 steps of method 1500 can be performed using Equation (2). In other embodiments, the processing steps 1508 and 1510 may be implemented using a directional filter, machine learning algorithm, or other suitable classification methodology that discriminates flow signal from projection artifact.

Following 1510 of method 1500, several options exist for visualization and quantification operations to be performed on the flow projection-suppressed data. One option, at 1512, is the generation of 2D en face angiograms for presentation in graphical format. Such 2D en face angiograms can be presented using a color-coding to scheme to convey depth information for blood flow (as in FIG. 11D), thereby increasing information content to facilitate interpretation (Zhang M et al, 2015 supra). Another possible option, at 1514, is to present structural OCT images with OCT angiography (flow) data overlaid such that a composite image is presented. These composite images may be presented as cross sectional B-scans to depict flow in different layers of the retina (as shown, for instance in FIG. 8A3). Further, the flow projection-suppressed OCT angiography data generated by method 1500 may be exported in a format that is amenable to storage and retrieval for further analysis (e.g., in a spreadsheet-readable format that may be retrieved for later statistical analysis).

Figure 16:
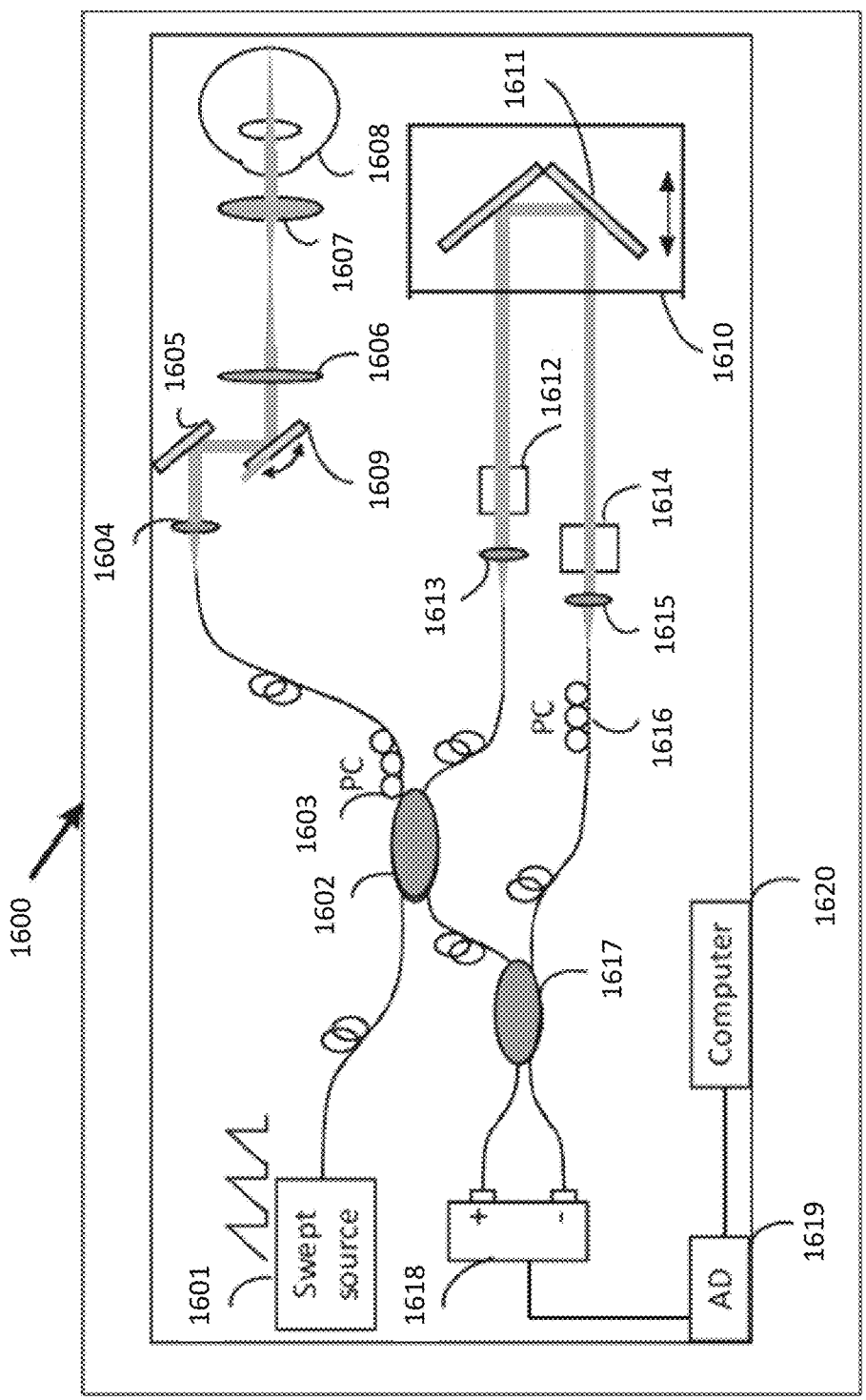
FIG. 16 schematically shows an OCT system that may be used to practice various embodiments disclosed herein.

FIG. 16 schematically illustrates an in vivo imaging system 1600 for collecting OCT image information. In some embodiments, the system 1600 may correspond to the system 1300 shown in FIG. 13. For example, the computer 1620 may correspond to the one or more processors 1304, and some or all of the remaining components of system 1600 may correspond to the OCT system 1302 of FIG. 13.

The system 1600 may be, for example, a high-speed swept-source OCT system 1600 (e.g., as described in B. Potsaid, B. Baumann, D. Huang, S. Barry, A. E. Cable, J. S. Schuman, J. S. Duker, and J. G. Fujimoto, "Ultrahigh speed 1050 nm swept source/fourier domain oct retinal and anterior segment imaging at 100,000 to 400,000 axial scans per second," Opt. Express 18(19), 20029-20048 (2010)) can used to demonstrate the methods described herein. High speed swept-source OCT system 1600 comprises a tunable laser 1601. For example, tunable laser 1601 (e.g., a tunable laser from Axsun Technologies, Inc, Billerica, Mass., USA) may have a wavelength of 1050 nm with 100 nm tuning range, a tuning cycle with a repetition rate of 100 kHz and a duty cycle of 50%. Such OCT system 1600 can produce a measured axial resolution of 5.3 µm (full-width-half-maximum amplitude profile) and an imaging range of 2.9 mm in tissue. Light from swept source 1601 can be coupled into a two by two fiber coupler 1602 through single mode optical fiber. One portion of the light (e.g., 70%) can proceed to the sample arm (i.e., the patient interface), and the other portion of the light (e.g., 30%) can proceed to the reference arm.

In the sample arm, a sample arm polarization control unit 1603 can be used to adjust light polarization state. The exit light from the fiber coupler 1602 can then be coupled with a retinal scanner whereby the light is collimated by sample arm collimating lens 1604 and reflected by mirror 1605 and two dimensional galvo scanner 1609 (e.g., an XY galvo-nanometer scanner). Two lenses, first lense 1606 (e.g., an objective lense) and second lense 1607 (e.g., an ocular lense) can relay probe beam reflected by galvo scanner 1609 into a human eye 1608. For example, a focused spot diameter of 18 µm (full-width-half-maximum amplitude profile) can be calculated on the retinal plane based on an eye model. The average light power (i.e., output power of the laser) onto a human eye can be 1.9 mW, which is consistent with safe ocular exposure limit set by the American National Standard Institute (ANSI).

The reference arm can comprise a first reference arm collimating lens 1613, a water cell 1612, a retro-reflector 1611, a glass plate 1614 and a second reference arm collimating lens 1615. Glass plate 1614 can be used to balance the dispersion between the OCT sample arm and reference arm. Water cell 1612 can be used to compensate the influence of dispersion in the human eye 1608. Retro-reflector 1611 can be mounted on a translation stage 1610 which can be moved to adjust the path length in the reference arm.

Light from the sample and reference arm can interfere at beam splitter 1617. A reference arm polarization control unit 1616 can be used to adjust the beam polarization state in the reference arm to maximum interference signal. The optical interference signal from beam splitter 1617 (e.g., a 50/50 coupler) can be detected by a balanced detector 1618 (e.g., a balanced receiver manufactured by Thorlabs, Inc, Newton, N.J., USA), sampled by an analog digital conversion unit 1619 (e.g., a high speed digitizer manufactured by Innovative Integration, Inc.) and transferred into computer 1620 for processing. For example, computer 1620 can be used for storing instructions for, and implementing, the methods described herein. Interference fringes, for example, can be recorded by analog digital conversion unit 1619 at 400 MHz with 14-bit resolution, with the acquisition driven by the optical clock output of tunable laser 1601. In such an exemplary setup, imaging system 1600, sensitivity can be measured with a mirror and neutral density filter at 95 dB, with a sensitivity roll-off of 4.2 dB/mm.

While a swept-source OCT system has been described above, the technology disclosed herein can be applied to any Fourier-domain OCT system. In Fourier-domain OCT systems the reference mirror is kept stationary and the interference between the sample and reference reflections are captured as spectral interferograms, which are processed by Fourier-transform to obtain cross-sectional images. In the spectral OCT implementation of Fourier-domain OCT, a broad band light source is used and the spectral interferogram is captured by a grating or prism-based spectrometer. The spectrometer uses a line camera to detect the spectral interferogram in a simultaneous manner. In the swept-source OCT implementation of Fourier-domain OCT, the light source is a laser that is very rapidly and repetitively tuned across a wide spectrum and the spectral interferogram is captured sequentially. Swept-source OCT can achieve higher speed and the beam can be scanned transversely more rapidly (with less spot overlap between axial scans) without suffering as much signal loss due to fringe washout compared to other Fourier-domain OCT systems. However, a very high speed spectral OCT system could also be utilized with the technology disclosed herein.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for suppressing shadowgraphic flow projection artifacts in an optical coherence tomography (OCT) angiography dataset, comprising:
   receiving a structural OCT dataset;
   calculating a set of decorrelation values from the structural OCT dataset;
   calculating a set of normalized decorrelation values from the set of decorrelation values based on respective reflectance amplitudes of decorrelation values of the set of decorrelation values;
   classifying the normalized decorrelation values as flow or projection artifact; and
   suppressing the decorrelation values that are associated with normalized decorrelation values classified as projection artifact, thereby generating a projection-suppressed OCT angiography dataset.

2. The method of claim 1, wherein calculating the set of decorrelation values from the OCT structural data is performed using an OCT angiography algorithm.

3. The method of claim 1, wherein calculating the set of decorrelation values from the OCT structural dataset is performed using a split-spectrum amplitude-decorrelation angiography (SSADA) algorithm.

4. The method of claim 1, wherein calculating the set of normalized decorrelation values is performed according to:

$$A = \frac{D}{\log(I)},$$

where A is a normalized decorrelation value of the set of normalized decorrelation values, D is a corresponding decorrelation value of the set of decorrelation values, and I is a reflectance amplitude of a corresponding voxel of the structural OCT dataset.

5. The method of claim 1, wherein classifying the normalized decorrelation values as flow or projection artifact comprises:
   selecting an A-scan from the set of normalized decorrelation values;
   identifying a set of successively larger normalized decorrelation values in an increasing depth direction along the selected A-scan; and
   classifying as flow the decorrelation values corresponding to the identified set of successively larger normalized decorrelation values.

6. The method of claim 5, wherein classifying the normalized decorrelation values as flow or projection artifact further comprises:
   classifying as projection artifact the decorrelation values corresponding to the normalized decorrelation values that are not included in the set of successively larger normalized decorrelation values.

7. The method of claim 1, wherein suppressing the decorrelation values associated with normalized decorrelation values classified as projection artifact is performed according to:

$$\begin{cases} C_n = D_n, & \text{if } A_n > (1+\alpha)\max(A_i), 1 \le i \le n-1 \\ C_n = 0, & \text{otherwise} \end{cases},$$

where i and n are the index of a voxel in an A-scan incrementing from a shallow end of the structural OCT dataset, $C_n$ is the normalized decorrelation value for index n, and $\alpha$ is a factor to account for noise in the structural OCT dataset.

8. A system for suppressing shadowgraphic flow projection artifacts in optical coherence tomography (OCT) angiography data, comprising:
   an OCT system configured to acquire a structural OCT dataset of a sample;
   a logic subsystem; and
   a data holding subsystem comprising machine-readable instructions stored thereon that are executable by the logic subsystem to:
      determine a set of decorrelation values from the structural OCT dataset;
      determine a set of normalized decorrelation values from the set of decorrelation values based on respective reflectance amplitudes of decorrelation values of the set of decorrelation values;
      classify the normalized decorrelation values as flow or projection artifact; and
      suppress the decorrelation values that correspond to normalized decorrelation values classified as projection artifact to generate a projection-suppressed OCT angiography dataset.

9. The system of claim 8, wherein the logic subsystem is to determine the set of decorrelation values from the OCT structural data using an OCT angiography algorithm.

10. The system of claim 8, wherein the logic subsystem is to determine the set of decorrelation values from the OCT structural dataset using a split-spectrum amplitude-decorrelation angiography (SSADA) algorithm.

11. The system of claim 8, wherein the logic subsystem is to determine the set of normalized decorrelation values according to:

$$A = \frac{D}{\log(I)},$$

where A is a normalized decorrelation value of the set of normalized decorrelation values, D is a corresponding decorrelation value of the set of decorrelation values, and I is a reflectance amplitude of a corresponding voxel of the structural OCT dataset.

12. The system of claim 8, wherein, to classify the normalized decorrelation values as flow or projection artifact, the logic subsystem is to:
   select an A-scan from the set of normalized decorrelation values;
   identify a set of successively larger normalized decorrelation values in an increasing depth direction along the selected A-scan; and
   classify as flow the decorrelation values corresponding to the identified set of successively larger normalized decorrelation values.

13. The system of claim 12, wherein, to classify the normalized decorrelation values as flow or projection artifact, the logic subsystem is further to:
   classify as projection artifact the decorrelation values corresponding to the normalized decorrelation values that are not included in the set of successively larger normalized decorrelation values.

14. The system of claim 8, wherein the logic subsystem is to suppress the decorrelation values that correspond to normalized decorrelation values classified as projection artifact according to:

$$\begin{cases} C_n = D_n, & \text{if } A_n > (1+\alpha)\max(A_i),\ 1 \le i \le n-1 \\ C_n = 0, & \text{otherwise} \end{cases}$$

where i and n are the index of a voxel in an A-scan incrementing from a shallow end of the structural OCT dataset, $C_n$ is the normalized decorrelation value for index n, and $\alpha$ is a factor to account for noise in the structural OCT dataset.

15. A method for suppressing shadowgraphic flow projection artifacts in an optical coherence tomography (OCT) angiography dataset, comprising:
   obtaining an OCT angiography dataset including decorrelation values associated with respective voxels that are arranged in a B-scan having a plurality of A-scans oriented in a depth direction;
   determining normalized decorrelation values associated with the respective voxels based on the decorrelation values and a reflectance of a corresponding voxel in an associated OCT structural dataset;
   identifying, within a first A-scan of the plurality of A-scans, a deepest voxel of the first A-scan for which all shallower voxels of the first A-scan have associated normalized decorrelation values that are less than a normalized decorrelation value of the deepest voxel;
   changing one or more of the decorrelation values associated with voxels of the first A-scan that are deeper than the deepest voxel to obtain a projection-suppressed OCT angiography dataset; and
   obtaining a flow image of a sample based on the projection-suppressed OCT angiography dataset.

16. The method of claim 15, wherein the changing the one or more decorrelation values comprises setting the decorrelation values for all voxels of the first A-scan that are deeper than the deepest voxel to zero.

17. The method of claim 15, wherein the B-scan is a first B-scan, and wherein the OCT angiography dataset is a 3-dimensional (3D) OCT angiography dataset including a plurality of B-scans including the first B-scan.

18. The method of claim 15, wherein the obtaining the OCT angiography dataset includes determining the OCT angiography dataset based on the associated OCT structural dataset.

19. The method of claim 18, wherein the OCT angiography dataset is determined based on the OCT structural dataset using a split-spectrum amplitude-decorrelation angiography (SSADA) algorithm.

20. The method of claim 15, wherein the determining the normalized decorrelation values is performed according to:

$$A = \frac{D}{\log(I)},$$

where A is a normalized decorrelation value of the a given voxel, D is a corresponding decorrelation value of the given voxel, and I is a reflectance amplitude of the corresponding voxel of the associated structural OCT dataset.

21. The method of claim 1, further comprising generating a flow image of a sample based on the projection-suppressed OCT angiography dataset.

22. The system of claim 8, wherein the logic subsystem is further to generate a flow image of a sample based on the projection-suppressed OCT angiography dataset.

* * * * *